US008815583B2

(12) United States Patent
Miller et al.

(10) Patent No.: US 8,815,583 B2
(45) Date of Patent: Aug. 26, 2014

(54) CELL LINES FOR EXPRESSING ENZYME USEFUL IN THE PREPARATION OF AMIDATED PRODUCTS

(75) Inventors: Duncan A. Miller, Morris Township, NJ (US); Nozer M Mehta, Randolph, NJ (US); Angelo P Consalvo, Monroe, NY (US)

(73) Assignee: Enteris BioPharma, Inc., Boonton, NJ (US)

(*) Notice: Subject to any disclaimer, the term of this patent is extended or adjusted under 35 U.S.C. 154(b) by 138 days.

(21) Appl. No.: 11/474,159

(22) Filed: Jun. 23, 2006

(65) Prior Publication Data
US 2006/0292672 A1 Dec. 28, 2006

Related U.S. Application Data

(60) Provisional application No. 60/693,612, filed on Jun. 24, 2005.

(51) Int. Cl.
*C12N 5/07* (2010.01)
*C12N 15/00* (2006.01)
*C12N 15/64* (2006.01)

(52) U.S. Cl.
USPC ............... 435/358; 435/320.1; 435/91.4

(58) Field of Classification Search
CPC ........ C12N 15/85; C12N 15/64; C12N 15/63; C12N 15/65
See application file for complete search history.

(56) References Cited

U.S. PATENT DOCUMENTS 5,089,397 A * 2/1992 Kushner et al. .............. 435/69.1
5,789,234 A * 8/1998 Bertelsen et al. ............ 435/354

FOREIGN PATENT DOCUMENTS

| WO | WO 86/02099 | 4/1986 |
| WO | 00/49162 A2 | 8/2000 |
| WO | 2004/061104 A2 | 7/2004 |
| WO | WO 2006/058225 | 6/2006 |

OTHER PUBLICATIONS

Chica et al. (Curr Opin Biotechnol. Aug. 2005; 16(4):378-84).*
Witkowski et al. (Biochemistry. Sep. 7, 1999; 38(36): 11643-50.*
Satani et al. (Protein Expression & purification 2003, 28 293-302).*
Mizuno, K. et al., "Cloning and Sequence of cDNA Encoding a Peptide C-Terminal α-Amidahng Enzyme from *Xenopus laevis*", Biochem Biophys. Res. Commun., vol. 148, No. 2, pp. 546-552, Oct. 29, 1987.
Ohsuye, K., et al., Cloning of a cDNA Encoding a New C-Terminal α-Amidating Enzyme Having a Putative Membrane-Spanning Domain from *Xenopus laevis* Skin:, Biochem. Biophys. Res. Commun., vol. 150, No. 3, pp. 1275-1281, Feb. 15, 1988.

Kolhekar, A.S. et al., "Peptidylglycine α-Hydroxylating Monooxygenase: Active Site Residues, Disulfide Linkages and Two-Domain Model of the Catalytic Core", Biochemistry, 1997, vol. 36, No. 36, pp. 10901-10909.
Kolhekar, A.S., et al., "Essential Features of the Catalytic Core of Peptidylglycine α-Hydroxyglycine α-Amidating Lyase", Biochemistry, 2002, vol. 41, No. 41, pp. 12384-12394.
Bertelsen, A.H., et al., "Cloning and Characterization of Two Alternatively Spliced Rat α-Amidating Enzyme cDNAs From Rat Medullary Thyroid Carcinoma", Arch. Biochem. Biophys., vol. 279, No. 1, pp. 87-96, May 15, 1990.
Jimenez N., et al., "Androgen-Independent Expression of Adrenomedullin and Peptidylglycine α-Amidating Monooxygenase in Human Prostatic Carcinomoa", Molecular Carcinogenesis, 38: 14-24 (2003).
Kolhekar, A.S., et al. "Neuropeptide Amidation in *Drosophila*: Separate Genes Encode the Two Enzymes Catalyzing Amidation", J. Neuroscience, 1997, 17(4):1363-1376.
Mizuno, K., et al., "Peptide C-Terminal α-Amidating Enzyme Purified to Homogeneity From *Xenopus laevis* Skin" Biochemical and Biophysical Research Co Cations, vol. 137, No. 3, pp. 984-991, Jun. 30, 1986.
Suzuki, K., et al., "Elucidation of Amidatin Reaction Mechanism by Frog Amidating Enzyme Peptidylglycine α-Hydroxylating Monooxygenase Expressed in Insect Cell Culture", The EMBO Journal, vol. 9, No. 13, pp. 4259-4265, 1990.
Betty A. Eipper, et al., "Peptidylglycine α-Amidating Monooxygenase: A Multifunctional Protein With Catalytic, Processing, and Routing Domains", Protein Science, 2, 489-497, 1993.
L'Houcine Ouafik, et al., The Multifunctional Peptidylglycine α-Amidating Monooxygenase Gene: Exon/Intron Organization of Catalytic, Processing and Routing Domains , Mol. Endo.,vol. 6, No. 10, pp. 1571-1584, 1992.
M. Satani et al., "Expression and characterization of human bifunctional peptidylglycine α-amidating monooxygnease", Protein Expression and Purification, 28:293-302 (2003).
Extended European Search Report dated Jun. 6, 2009 in corresponding European Patent Application No. 06785535.3-2401.

(Continued)

*Primary Examiner* — Tekchand Saidha
*Assistant Examiner* — Younus Meah
(74) *Attorney, Agent, or Firm* — Greenberg Traurig, LLP; David J. Dykerman; Danielle T. Abramson

(57) ABSTRACT

Cell lines are provided for expressing peptidylglycine alpha-amidating monooxygenase (PAM), or one of its two catalytic domains. High levels of enzyme expression are achieved while utilizing a non-animal source, low protein tissue culture medium. A robust two-step downstream purification results in high enzyme purity. Resulting PAM, or its PHM catalytic domain, is used to catalyze the enzymatic conversion of X-Gly to X-alpha-hydroxy-Gly or X—$NH_2$ (X being a peptide or any chemical compound having a carbonyl group to which a glycine group can be covalently attached). Methods of preparing preferred cell lines are also set forth.

15 Claims, 15 Drawing Sheets

(56) References Cited

OTHER PUBLICATIONS

Miller, D.A., et al.: Characterization of a Bifunctional Peptilvl rllcine alpha-amidating Enzyme Expressed in Chinese Hamster Ovary Cells, Archives of Biochemistry Biophysics, vol. 298, No. 2, pp. 380-388, Nov. 1, 1992, XP024760776, ISSN 0003-9861, abstract.
Takahashi, K. et al.: "Expression and characterization of from peptidylglycine alpha-hydroxylating monooxygenase", Protein Expression and Purification, vol. 27, No. 1, Jan. 2003, pp. 35-41, XP002530285, ISSN: 1046-5928, abstract.
Friedman, J.S., et al.: High Expression In Mammalian Cells Without Amplification, Bio/Technology, vol. 7, No. 4, Apr. 1, 1989, pp. 359-362, XP008043216, ISSN: 0733-222X, abstract.
Declaration of Ronald S. Levy, Ph.D. signed Aug. 12, 2010.

* cited by examiner

*Plasmid Map of PHS1*

*Plasmid Map of pAE73*

*Dissolved Oxygen Concentration And α-AE Productivity In Spinner Flasks*

*pH Profile Of Stirred Tank Bioreactors And Spinner Flasks Without pH Control*

*pH Effect On UGL 73-26/M α-AE Productivity In Stirred Tank Bioreactors*

*SDS PAGE Of Purified PAM Enzyme*
Lane 1-α-AE reference standard, Lane 2 -Broad Range Molecular Weight Markers, Lane 3 – Clarified Harvest, Lane 4 - TFF 1 retentate, Lane 5 - TFF 1 retentate, Lane 6 – Q-Sepahrose FF eluate, Lane 7 – Q-Sepharose FF eluate, Lane 8 – Phenyl Sepharose FF eluate, Lane 9 – Phenyl Sepharose eluate, Lane 10 – TFF 2 retentate.

*Densitometry Scan Of SDS PAGE Gel and Calculation of Percent Peak Areas*

*Process Flow Diagram For Production Of α-AE*

CELL LINES FOR EXPRESSING ENZYME USEFUL IN THE PREPARATION OF AMIDATED PRODUCTS

CROSS REFERENCE TO A RELATED APPLICATION

This application claims priority of U.S. Provisional Application Ser. No. 60/693,612 filed Jun. 24, 2005, the disclosure of which is incorporated by reference herein.

FIELD OF THE INVENTION

The present invention relates to recombinant expression vectors, and to cell lines, for the expression of peptidylglycine alpha-amidating monooxygenase (PAM or α-AE), or one of its two catalytic domains. The invention also relates to the use of such PAM (or one of its catalytic domains) to catalyze the enzymatic conversion of X-Gly to X-alpha-hydroxy-Gly or X—NH$_2$ (X being a peptide or any chemical compound having a carbonyl group to which a glycine group can be covalently attached). The invention further relates to the preparation of preferred cell lines. In some embodiments CHO K1 hosts are utilized. In some embodiments, expression vectors include a human metallothionin IIA promoter and/or an SV40 enhancer.

DESCRIPTION OF THE RELATED ART

Numerous human hormones, growth factors, cytokines, neurotransmitters, derivatized fatty acids, and other important biological compounds have amino acid or peptide as a substantial part of their molecular structures. Many diseases respond positively to raising the level of these biological compounds in patients. Therapeutically effective amounts of such biologically relevant compounds may be administered to patients in a variety of ways. Thus, efficient cost-effective manufacturing processes for such compounds are very important. This is especially true when the biological compounds are prepared in dosage form for oral delivery, a usually preferred mode of administration despite lower bioavailability relative to other modes of administration.

Mammalian cells and other eukaryotes can perform certain post-translational processing procedures, while prokaryotes cannot. Certain prokaryotes, such as *E. coli*, are widely employed as hosts for the production of mammalian proteins via recombinant DNA (rDNA) technology because they can be readily grown in batch fermentation procedures and because they are genetically well-characterized. However, many mammalian proteins require some type of post-translational processing. If these proteins are produced by genetic engineering of *E. coli*, for example, the post-translational processing must often be accomplished using complex, in vitro chemical procedures which are cost-prohibitive for large-scale production applications. Even when peptides are recombinantly produced using mammalian hosts, it is often desirable to efficiently produce a precursor which is only later subjected to further modification.

One type of such further processing activity involves the specific amidation of the carboxy-terminal amino acid of a peptide or protein. Many naturally-occurring hormones and peptides contain such a modification, which is often essential if the protein is to be biologically active. An example is calcitonin, where the substitution of a non-amidated proline residue for the amidated proline of the native form results in a very significant reduction in biological activity. Other biological peptides requiring post-translational amidation for full activity include but are not limited to growth hormone releasing factor, other calcitonins, calcitonin gene-related peptide, secretin, Peptide YY and the like.

The polypeptide sequences for many important biological proteins which require amidation for maximal efficacy, may be manufactured, for example, by genetic engineering techniques. However, the important and sometimes essential carboxy terminal amidation must often be performed in vitro. It is desirable to avoid costly and cumbersome chemical amidation techniques at this point, and is therefore desirable to utilize an amidating enzyme to perform the specific amidation. The specific amidation of the carboxy-terminal amino acid of a protein is frequently catalyzed by alpha-amidating enzymes.

Peptidylglycine α-amidating monooxygenase (PAM) catalyzes the conversion of a peptide substrate to an amidated peptide product. The conversion is a two-step reaction. PAM has two catalytic domains: peptidylglycine α-hydroxylating monooxygenase (PHM) catalyzes Step 1 (conversion of substrate to intermediate) and peptidylglycine α-hydroxyglycine α-amidating lyase (PAL) catalyzes Step 2 (conversion of intermediate to product). Full length PAM is bifunctional and catalyzes both steps. Step 2 may also be efficiently accomplished non-enzymatically if the intermediate is contacted with a Lewis base.

In nature, approximately 50% of peptide hormones and neurotransmitters are amidated by PAM in the foregoing manner. PAM activity has been recognized in numerous diverse species, PAM tends to have significant structural homology among species as diverse as rat, cow and frog. It is also known that PAM's function, substrate and cofactors are similar (frequently identical) across species. The substrate is a compound, often a peptide, having a glycine residue with a free carboxyl group. PAM-catalyzed amidation reactions are well known in the art. For example, one is described in detail in U.S. Pat. No. 6,103,495 where a peptidylglycine α-amidating monooxygenase is used to catalyze the conversion of a glycine-extended salmon calcitonin precursor to authentic salmon calcitonin, amidated at its C-terminus (i.e., having an amino group in place of the precursor's C-terminal glycine).

Sources of PAM and cell lines expressing PAM are known in the art. Large scale PAM-catalyzed production of amidated peptides requires a stable high-yield source of PAM for best cost-effectiveness. Additionally, because PAM is frequently utilized for the production of potential human pharmaceutical products, it is important that the system for PAM production (both the PAM-expressing cell line, and the culture media in which it is grown) introduce as few impurities as possible during PAM expression. Of particular concern, is minimizing the use of mammalian proteins in order to avoid the risk of transmissible spongiform encephalopathies (TSEs). Mammalian protein growth factors in the culture media (undesirable from a TSE standpoint) may nonetheless be useful in aiding the survival and product expression of PAM-expressing cell lines. Thus, there is a need in the art for PAM-expressing (or PHM-expressing) cells that provide strong expression and show good stability and survival even in the absence of mammalian proteins that might otherwise be required in the media.

SUMMARY OF THE INVENTION

It is therefore an object of the present invention to provide PAM-expressing or PHM-expressing cells which are hardy enough to have good survival rates and good expression yields in media substantially devoid of the types of mammalian proteins and other impurities that could be problematic when the enzyme is later used in the manufacture of products (e.g. manufacture of amidated pharmaceutical products).

It is a further object of the invention to provide PAM-expressing or PHM-expressing cells that do not themselves co-express significant undesirable impurities.

It is a further object to provide PAM-expressing or PHM-expressing cells that provide good expression yields.

It is a further object to provide expression vectors useful in such cells.

It is a further object to provide good techniques for tranfecting and selecting such cells.

It is a further object to provide high activity and high purity PAM or PHM for use in enzymatic reactions, and to thereby provide good enzymatic reactions and resulting amidated product.

These and other objects are provided by the inventions disclosed herein.

In one embodiment, the invention provides a CHO K1 cell transfected with an expression vector for expressing peptidylglycine alpha-amidating monooxygenase.

In another embodiment, the invention provides a recombinant expression vector having a coding region with nucleic acids encoding peptidylglycine alpha-amidating monooxygenase, operably linked to a control region including a ribosome binding site, a promoter and an SV40 enhancer upstream of said promoter.

In another embodiment, the invention provides a recombinant expression vector having a coding region with nucleic acids encoding peptidylglycine alpha-amidating monooxygenase, operably linked to a control region including a ribosome binding site and, a human metallothionin IIA promoter.

In another embodiment, the invention provides a method of preparing a cell line for the expression of peptidylglycine alpha-amidating monooxygenase, said method comprising the steps of:

(A) Transfecting potential host cells in the presence of first, second and third expression vectors, wherein said first vector includes a coding region encoding a first selectable marker, wherein said second vector includes a coding region encoding a second selectable marker, wherein said third vector includes a coding region encoding peptidylglycine alpha-amidating monooxygenase, wherein the concentration ratio of said third vector to said first vector is at least 3:1, and wherein the concentration ratio of said third vector to said second vector is at least 3:1;

(B) Subjecting the cells resulting from step (A) to selectable pressure to select cells that have been transfected with said first vector;

(C) Subjecting the cells resulting from step (B) to selectable pressure to select cells that have been transfected with said second vector;

(D) Subjecting the cells resulting from step (C) to limiting dilution and selecting cells expressing peptidylglycine alpha-amidating monooxygenase.

In another embodiment, the invention provides cell line UGL 73-26/M.

In another embodiment, the invention provides peptidylglycine alpha-amidating monooxygenase expressed by cell line UGL 73-26/M.

In another embodiment, the invention provides a method of purifying peptidylglycine alpha-amidating monooxygenase following expression and secretion into culture media, wherein said method includes the steps of:

(A) subjecting an impure sample of peptidylglycine alpha-amidating monooxygenase to anion exchange chromatography wherein elution is isocratic;

(B) subjecting the eluant of step (A) to hydrophobic interaction chromatography, wherein ammonium sulfate is not used and wherein elution is isocratic.

In another embodiment, the invention provides a CHO K1 cell transfected with an expression vector for expressing peptidylglycine alpha-hydroxylating monooxygenase.

In another embodiment, the invention provides a recombinant expression vector having a coding region with nucleic acids encoding peptidylglycine alpha-hydroxylating monooxygenase, operably linked to a control region including a ribosome binding site, a promoter and an SV40 enhancer upstream of said promoter.

In another embodiment, the invention provides a recombinant expression vector having a coding region with nucleic acids encoding peptidylglycine alpha-hydroxylating monooxygenase, operably linked to a control region including a ribosome binding site and, a human metallothionin IIA promoter.

In another embodiment, the invention provides a method of preparing a cell line for the expression of peptidylglycine alpha-hydroxylating monooxygenase, said method comprising the steps of:

(A) Transfecting potential host cells in the presence of first, second and third expression vectors, wherein said first vector includes a coding region encoding a first selectable marker, wherein said second vector includes a coding region encoding a second selectable marker, wherein said third vector includes a coding region encoding peptidylglycine alpha-hydroxylating monooxygenase, wherein the concentration ratio of said third vector to said first vector is at least 3:1, and wherein the concentration ratio of said third vector to said second vector is at least 3:1;

(B) Subjecting the cells resulting from step (A) to selectable pressure to select cells that have been transfected with said first vector;

(C) Subjecting the cells resulting from step (B) to selectable pressure to select cells that have been transfected with said second vector;

(D) Subjecting the cells resulting from step (C) to limiting dilution and selecting cells expressing peptidylglycine alpha-hydroxylating monooxygenase.

In another embodiment, the invention provides a method of purifying peptidylglycine alpha-hydroxylating monooxygenase following expression and secretion into culture media, wherein said method includes the steps of:

(A) Subjecting an impure sample of peptidylglycine alpha-hydroxylating monooxygenase to anion exchange chromatography wherein elution is isocratic;

(B) Subjecting the eluant of step (A) to hydrophobic interaction chromatography, wherein ammonium sulfate is not used and wherein elution is isocratic.

The desired enzyme is expressed by the cells and cell lines of the invention, and in preferred embodiments purified in accordance with a purification techniques of the invention. Reactions are then performed in the presence of the enzyme starting with precursors which have a glycine residue, in free acid form and attached to a carbonyl group. Reaction conditions and co-factors are known in the art. Examples 1 and 2, herein, show a typical amidation reaction and purification of amidated product. Preferred amidated products result. When peptidyl alpha-hydroxylating monooxygenase is utilized, an intermediate results which requires further reaction with either a Lewis base or peptidyl alpha-hydroxy glycine alpha-amidating lyase to form the amidated product.

When enzyme-producing cell lines such as those discussed herein express and secrete enzyme into culture media, a series of steps may be followed, in certain embodiments, to purify the enzyme. A harvesting step separates conditioned medium from cells. A first tangential flow filtration (concentration, diafiltration) removes low molecular weight components. An anion exchange chromatography step and a hydrophobic interaction chromatography step are utilized primarily for purification from protein impurities and medium components. A final tangential flow filtration, concentration and buffer exchange prior to virus filtration are desirably employed prior to storage. Improved anion exchange chromatography and hydrophobic interaction chromatography are claimed herein.

It has surprisingly been found that desirably stable CHO K1 cells may be used in the context of the invention despite the presence of an endogenous dihydrofolate reductase gene. The endogenous gene did not significantly interfere with methotrexate selection based on a selectable marker having a dihydrofolate reductase gene.

Co-transfecting the PAM gene with two selectable markers on independent vectors, as described herein, is believed to significantly increase the chances of co-amplification occuring at more desirable parts of the genome.

When an SV40 enhancer is used, it is understood that the enhancer may be used together with any transcriptional promoter including but not limited to the SV40 transcriptional promoter, the preferred metallothionin IIA promoter discussed herein and the like.

Peptidylglycine alpha-amidating monooxygenase expressed and purified in accordance with the present invention is substantially free of undesirable protease activity and is suitable for efficient alpha-amidation of substrate as described herein.

A preferred cell line discussed herein, UGL 73-26/M, showed a good longevity profile, and is hence believed to be particularly useful for scale-up where stability is of significant importance.

Likewise, the preferred purification techniques discussed herein provide scalable characteristics and significant product purity. Specifically, isocratic elution is used which significantly simplifies fraction collection. Prior art use of ammonium sulfate in connection with hydrophobic interaction chromatography is desirably avoided because ammonium sulfate can cause precipitation and inactivation of the enzyme.

By analogy, it is expected that the inventions described herein will be beneficial with regard to peptidylglycine alpha-hydroxylating monooxygenase, as they have been beneficial with peptidylglycine alpha-amidating monooxygenase.

One or more of the preferences stated herein may be used in combination. For example, and not by way of limitation, preferred promoters may be used together with preferred enhancers and/or with preferred host cells.

When (A) PHM and (B) either PAL or a Lewis base, are used for amidation in lieu of PAM, the PHM and PAL (where used) may be obtained in a number of ways. Some are set forth below.

PHM
Express Naturally Occurring Forms of the PAM Gene that when Expressed Contain Only the PHM Activity One enzyme derived from frog is a naturally occurring PHM enzyme. See Mizuno et al (1986), "Peptide C-Terminal a-Amidating Enzyme Purified to Homogeneity From *Xenopus laevis* Skin" *Biochem Biophys. Res. Commun.*, 137 (3) 984-991, which was later found to be a PHM rather than full-length PAM. See Suzuki et al (1990), EMBO 9 (13) 4259-4265.

Express a Full Length PAM and Cleave

A specific protease could be used to cleave the PAM enzyme at a site between the PHM activity and the PAL activity, for example a dibasic cleavage site. The PHM catalytic domain can then be obtained by purification. For example, Ouafik et al, (1992) "The Multifunctional Peptidylglycine α-Amidating Monooxygenase Gene: Exon/Intron Organization of Catalytic, Processing, and Routing Domains" *Molecular Endocrinology* 6 (10) 1571-1584 describes the location of the two catalytic domains in a rat-derived PAM, and notes that "endoproteolytic cleavage at a paired basic site can separate the two catalytic domains." See also Eipper et al (1993), "Peptidylglycine α-Amidating Monooxygenase: A Multifunctional Protein With Catalytic, Processing, and Routing Domains" *Protein Science* 2, 489-497.

Introduce a stop codon in PAM or a point mutation that alters the reading frame As an alternative, translation stop codons (TAA, TAG, TGA) can be introduced in any PAM cDNA from any species between the two functional domains of PAM (PHM and PAL), or a point mutation in such a location could be introduced to alter the reading frame.

Reengineer an Expression Vector with Only a PHM cDNA

Using PCR, a truncated PAM gene encoding only the PHM domain could be synthesized and put into an expression vector downstream of a promoter or enhancer/promoter sequence.

Set forth below are additional references for different types of PAM enzyme and its catalytic domains:

Mizuno, K. et al., (1987) "Cloning and sequence of cDNA encoding a peptide C-terminal α-amidating enzyme" from *Xenopus Laevis Biochem Biophys. Res. Commun.*, 148 (2) 546-552.

Ohsuye, K., et al., (1988) "Cloning of a cDNA encoding a new C-terminal α-amidating enzyme having a putative membrane-spanning domain" from *Xenopus Laevis Biochem. Biophys. Res. Commun.*, 150 (3) 1275-1281.

Koljekar, A. S., et al., (1997) "Peptidylglycine α-amidating hydroxylating monooxygenase: active site residues, disulfide linkages and tow-domain model of the catalytic core", *Biochemistry* 36:13901-13909.

Koljekar, A. S., et al., (2002) "Essential features of the catalytic core of Peptidylglycine α-hydroxyglycine α-amidating lyase", *Biochemistry*, 41:12384-12394. Bertelsen, A. H., et al., (1990) "Cloning and characterization of two alternatively spliced rat α-amidating enzyme cDNAs from rat medullary thyroid carcinoma", *Arch. Biochem. Biophys.*, 279 (1) 87-96.

Jimenez N., et al., (2003) "Androgen-independent expression of adrenomedullin and peptidylglycine α-amidating monooxygenase in human prostatic carcinoma", *Molecular Carcinogenesis* 35: 14-24.

PAL
Express Naturally Occurring Forms of PAL

The two catalytic domains of PAM are encoded by separate genes in *Drosophila* and in cnidarians (sea anemone). Therefore, the gene encoding PAL from these species can be expressed when put into an expression vector downstream of a promoter or enchancer/promoter sequence. See Kolhekar, A. S., et al. (1997) "Neuropeptide Amidation in *Drosophila*: Separate Genes Encode the Two Enzymes Catalyzing Amidation" *J. Neuroscience* 17(4):1363-1376.

Express a Full Length PAM and Cleave

Full length bifunctional PAM could be expressed, and cleavage at a specific protease site can be performed in between the PHM and PAL domains and/or within the PHM domain to inactivate the PHM. Any suitably specific protease could be used to disassociate the PHM activity from the PAL activity, for example, a dibasic cleavage site. The PAL activity/protein can be further purified. A similar procedure and a location for the dibasic cleavage site are described above in connection with obtaining PHM.

Reengineer an Expression Vector with Only a PAL cDNA

Using PCR a truncated PAM gene encoding only the PAL domain could be synthesized and put into an expression vector downstream of a promoter or enhancer/promoter sequence.

Other features and advantages of the present invention will become apparent from the following description of the invention which refers to the accompanying figures, charts, tables, and the like.

DETAILED DESCRIPTION OF EMBODIMENTS OF THE INVENTION

Figure 1:
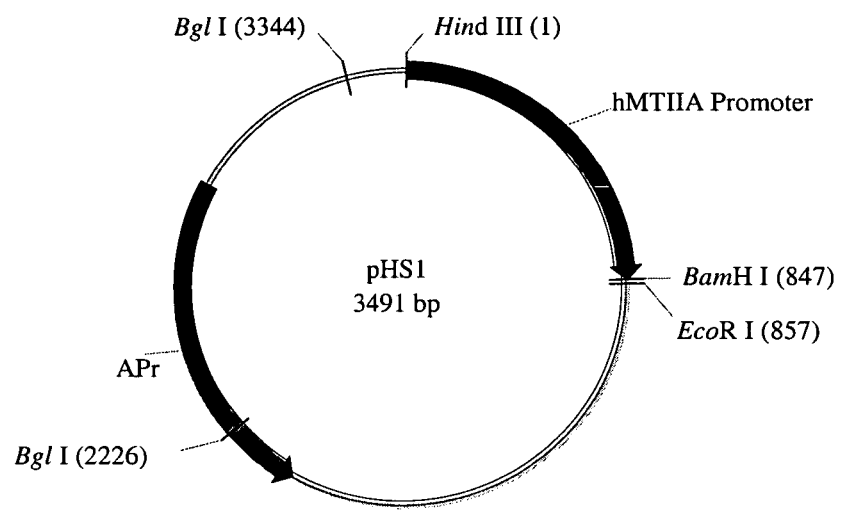
FIG. 1 is a plasmid map of pHS1.

A PAM-expressing cell line in accordance with the invention (internally designated UGL 73-26/M MWCB 00) was deposited with the American Type Culture Collection (ATCC), 10801 University Boulevard, Manassas Va., 20110-2209, U.S.A., on or about Jun. 10, 2005, pursuant to the Budapest Treaty on the International Recognition of Deposits of Microorgansims for Purposes of Patent Procedure. The ATCC accession number is PTA 6784. This deposited cell line is subject to the Regulations promulgated under this Treaty, and samples will be made available at the time, and under the conditions required by, the Treaty, and in compliance with the patent laws and regulations of the Treaty signatories. For example, upon issuance of a U.S. patent based on this application or any other U.S. application claiming priority hereof or making reference hereto, all restrictions upon availability of the deposited material will be irrevocably removed to the extent required by the Budapest Treaty or by 35 U.S.C. §112.

The construction of a PAM-expressing vector of the invention is described in detail infra. In the plasmid maps, herein, The region marked "alpha amidating enzyme" (see e.g., FIG. 5, the plasmid map of pAE 73) has the nucleotide sequence set forth as SEQ ID NO. 1 appended hereto, and encodes a 715 amino acid primary translation product set forth as SEQ ID NO. 2 appended hereto. That translation product includes a signal peptide at amino acids 1-25, a pro-region at 26-41, and a mature peptidylglycine alpha-amidating monooxygenase at 42-715. Most of the enzyme expressed and purified in accordance with the invention continues to include the pro-region, and has proven to be very effective.

Detailed below are examples of a preferred PAM-expressing cell line, its fermentation, process development, purification and use.

As discussed in more detail, infra, a PAM gene was cloned into the pSV402MT expression vector to create the PAM expression plasmid pAE73. CHO K1 cells were transfected with pAE73 DNA. Following a dual selection process and limiting dilution cloning a CHO cell line was further amplified with increasing concentrations of methotrexate. The adherent cell line 73-26 was converted to a selection free, serum-free suspension culture, UGL 73-26/M. A UGL 73-26/M MCB and MWCB were created at BioReliance Corp. Both the MCB and MWCB have been fully characterized and are deemed acceptable for production of PAM in a GMP facility. The UGL 73-26/M cell line has been adapted to grow in a stirred tank bioreactor. Fermentation development has led to defining an inoculum process that takes 14 days in spinner flasks. The fermentation/cell culture phase is a 17 day process. The key parameters of the fermentation process are as follows: glucose addition (2 g/L) on days 5, 10 and 14, dissolved oxygen concentration ≥70%, the pH of the fermentation to reach its natural set point, and a protein-free, non-animal sourced tissue culture media, Sigma C5467, supplemented with glutamine to a final concentration of 2 mM. A simple and robust downstream purification process was developed for the PAM from C5467 conditioned CHO medium. A four-fold increase in purity and 40% overall recovery of active enzyme are routinely achieved after purification. The process utilizes conventional filtration systems and bioprocess chromatography resins that are amenable to scale-up to the manufacturing level. The entire cell culture fermentation and downstream purification processes have been scaled to a 10 L pilot plant/manufacturing level. The process as described should be amenable to a validatable manufacturing process for the production of large quantities of PAM.

A CHO cell line was developed that expresses large amounts of PAM, UGL 73-26/M. The cell culture process developed for UGL 73-26/M was in a non-animal protein sourced media. A simple batch cell culture process was preferred. The objective of the purification scheme was to develop a robust and scalable process with good yields of catalytically active enzyme.

Vector Construction

The creation of the expression vector used to generate the cell line, pAE73 was based on results from the work of Friedman et al. Bio/Technology 7:359-362 (1989). Following the process described in this article, we proceeded to create the pAE73 expression vectors for testing. The major components of each vector are the human metallothionein hA (hMTIIA) promoter (located in pHS1, received from M. Karin), the SV40 enhancer (derived from pSV40, ATCC), and the α-amidating enzyme gene described herein.

Derivation of pAE73 pHS1

Figure 2:
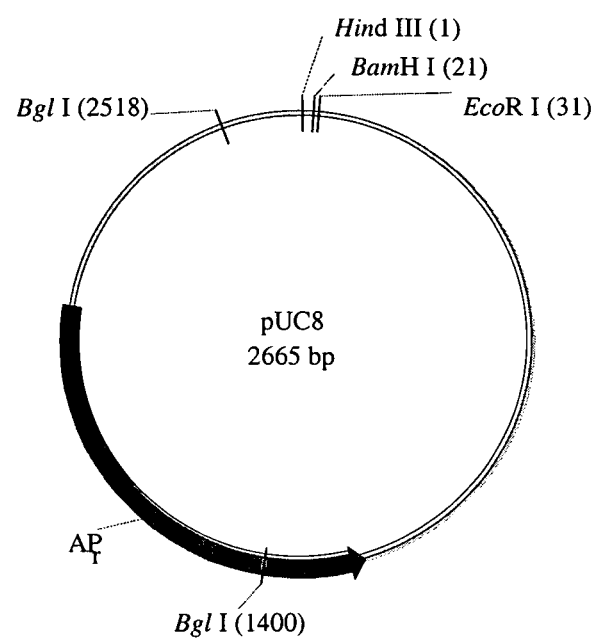
FIG. 2 is a plasmid map of pUC8.
Figure 3:
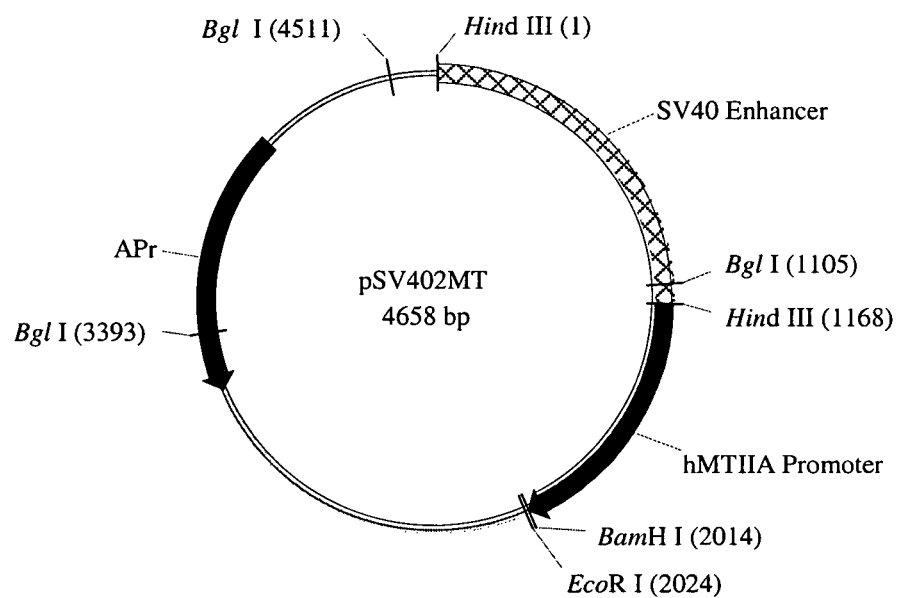
FIG. 3 is a plasmid map of pSV402MT.
Figure 4:
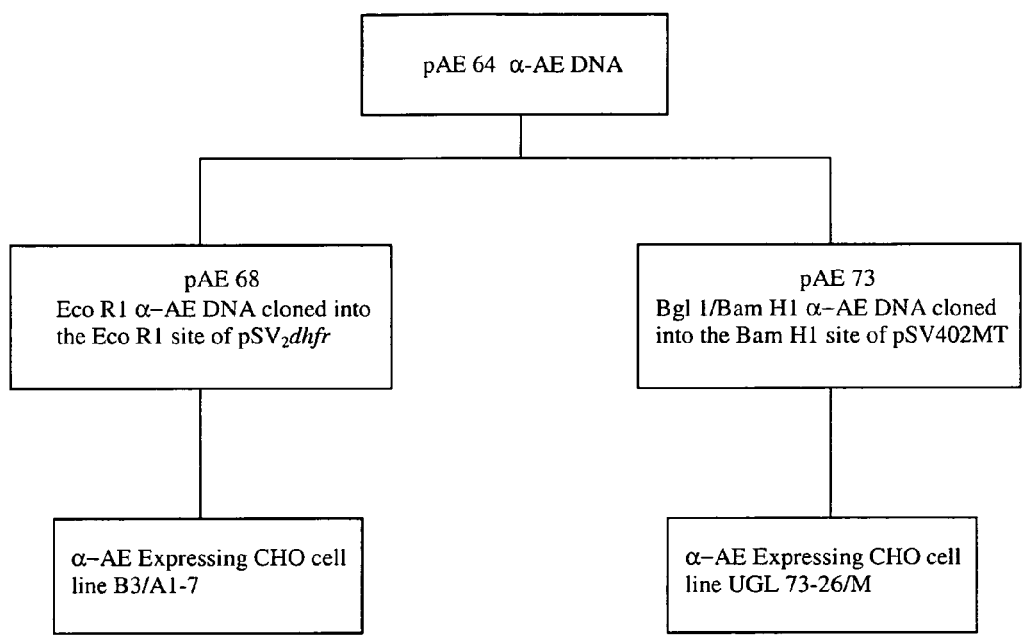
FIG. 4 is a derivtion of α-AE cDNA Gene Sequence.

The starting plasmid used in the creation of pAE73 was the plasmid pHS1 (FIG. 1), a gift from M. Karin at UCSD in February 1990. pHS1 was derived in Dr. Karin's laboratory by splicing into pUC8 (FIG. 2) the human metallothionein IIA promoter. The 846 bp Hind III/Bam H1 fragment was cloned into the Hind III-Bam H1 site of the pUC8 multiple cloning site (MCS). The resulting plasmid, pHS1, has the human metallothionein IIA promoter inserted in the multiple cloning site.

pSV40MT and pSV402MT pHS1 was converted into the expression vector pSV401MT or pSV402MT (FIG. 3) by inserting the SV40 enhancer upstream of the human metallothionein promoter. The SV40 DNA fragment was prepared by digesting pSV40 plasmid DNA with Hind III. The 1167 bp Hind III fragment was cloned into the Hind III site of pHS1. The SV40 enhancer sits asymmetrically within the Hind III DNA fragment thus locating the enhancer either close to or far away from the hMTIIA promoter. The orientation of the Bgl I site within the SV40 enhancer relative to that in the lac Z gene in the original plasmid determines the plasmid designation. pSV401MT has the SV40 enhancer far away from the hMTIIA promoter and pSV402MT has the SV40 enhancer close to the hMTIIA promoter. pSV402MT was chosen for further vector construction.

pAE 73 pAE73 was prepared by cloning the alpha-amidating enzyme gene (SEQ ID NO 1) into the Bam H1 site of pSV402MT. The 2870 bp α-AE gene fragment was isolated following digestion of pAE64 with Bgl 1 and Bam H1 DNA restriction endonucleases. The pAE64 plasmid contains a PAM gene downstream of the SV40 promoter/enhancer that has been modified to express a soluble 75 kDa PAM protein. This PAM DNA sequence has been used in another CHO expressing cell line, UGL B3/A1-7, to express the 75 kDa PAM protein. Derivation of the PAM gene sequence is shown in FIG. 4.

The 2870 bp DNA fragment was purified and the Bgl 1 end of the fragment modified with two complimentary DNA oligonucleotide fragments (AE96/AE97) that converted the Bgl 1 end of the fragment to a new Bam H1 end.

```
AE96 (+) 23 5' GATCCATCGATCGCACTAGT-    (SE-
GCC 3'                                   Q ID NO: 3

AE97 (-) 16 5' ACTAGTGCGATCGATG 3'       SEQ ID NO:
                                         4)
```

Figure 5:
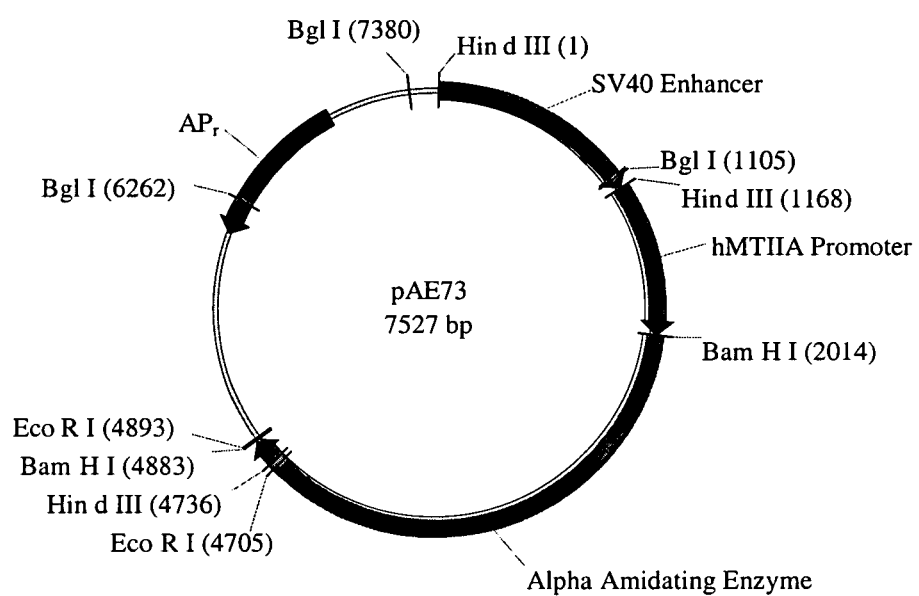
FIG. 5 is a plasmid map of pAE73.

The modified PAM DNA fragment was cloned into the Bam H1 site of the expression vector, pSV402MT. The PAM DNA fragment with two Bam H1 ends could ligate into the expression vector in either the sense or antisense orientation, therefore the orientation of the PAM gene was determined by the restriction digest mapping of the plasmid with Eco R1. An Eco R1 site in both the PAM gene and the expression vector allows for a simple analysis of plasmid DNA. The plasmid with the PAM in the correct orientation was designated as pAE73, and it's plasmid map is shown in FIG. 5

Creation of an α-Amidating Enzyme Expressing Cell Line
Transfection and Cloning

Three plasmids were used in the transformation of CHO K1 cells: pAE73, pSV$_2$neo and pSV$_2$dhfr. The plasmids pSV$_2$neo and pSV$_2$dhfr (both obtained from the ATCC) were used because incorporation of these plasmids by transfected cells allows for easy selection of transformed cell lines. The plasmid pSV$_2$dhfr was also specifically chosen because incorporation of the SV40 promoter/dhfr DNA into the CHO genome allows for selective amplification of that gene and other proximal genes. The gene to be co-amplified was the α-amidating enzyme gene carried in the plasmid pAE73. CHO Ka1 cells were transformed by calcium phosphate precipitation of plasmid DNA. The plasmids were transfected into the cells in a ratio of 10:1:1, pAE73:pSV$_2$neo:pSV$_2$dhfr. 20 μg pAE73 was added per 100 mm dish. Two days after the transfection, the cells were grown under selective pressure in a medium containing 250 mg/L G418 to allow for only transformed cells to survive. CHO cell growth in this medium would require stable incorporation of the pSV$_2$neo plasmid. Methotrexate was added to the growth medium 27 days after transfection, once stable growth was established in G418 selective media. The G418 pools of transformed cells were grown in media containing 100 nM, 500 nM, 1 μM or 5 μM methotrexate and 250 mg/L G418. Two weeks later (six weeks post transfection) isolated foci of cells could be established from cells grown in 5 μM methotrexate+G418 media by cloning cylinders. An attempt was made to establish cell lines from twenty-five foci by this method, but cells from only two foci grew after transfer and this technique was abandoned. Limiting dilution cloning, 0.5 cells/well, was initiated at the same time from cells grown in media containing 1 μM methotrexate+G418. Transformed cells grown in lower concentrations of methotrexate were abandoned. Three weeks after starting limiting dilution cloning isolates were transferred to 24-well plates and then to 100 mm dishes for expanded growth within 2-3 days. Ten weeks after initial transfection of CHO K1 cells, one of the isolates designated 73-26 was established. The cell line was cryopreserved and α-amidating enzyme expression assessed. 73-26 was one of the best producing cell lines at this juncture producing 6953 U/10$^6$ cells/day.

Amplification of Cell Line 73-26

The primary clone of 73-26 was passaged to yield an established cell line maintained in media containing 1 μM methotrexate+G418. The purpose of choosing the pSV$_2$dhfr plasmid for transfection was not only because it provided a second selection method to identify transformed cell lines but because it has been widely established that the dhfr mini gene is amplified when cells are grown at high concentrations of methotrexate. Unigene Laboratories had previous experience with cell lines transformed with this plasmid showing that concentrations of 20-50 μM methotrexate may be required to elicit the maximum production of α-amidating enzyme. The α-amidating enzyme cell line 73-26 was split directly into media containing 1 μM, 20 μM, or 50 μM methotrexate. All media also contained G418 as a second method of selection. The progression of α-amidating enzyme expression of this cell line at various time intervals is shown in Table 1.

TABLE 1

Amplification and Expansion of CHO Cell Line 73-26

| Date | Cell Line | Methotrexate (μM) | α-AE (U/10$^6$ cells/Day) | Relative Activity to B3/A1–7 Control | Comments |
| --- | --- | --- | --- | --- | --- |
| Aug. 19, 1991 | | | | | cell line switched to media with increased concentrations of methotrexate |

TABLE 1-continued

Amplification and Expansion of CHO Cell Line 73-26

| Date | Cell Line | Methotrexate (μM) | α-AE (U/$10^6$ cells/Day) | Relative Activity to B3/A1–7 Control | Comments |
|---|---|---|---|---|---|
| Sep. 26, 1991 | 73-26 | 1 | 15138 | | |
| | 73-26 | 20 | ND | | cell line growth slow |
| | 73-26 | 50 | ND | | cell line growth slow |
| Oct. 28, 1991 | 73-26 | 1 | 25000 | | |
| | 73-26 | 20 | 6923 | | |
| | 73-26 | 50 | 114162 | | |
| | 73-26 | | | | |
| Nov. 21-22, 1991 | B3-A1/7 | | 5714/4087 | | |
| | 73-26 | 1 | 73099/30065 | 16.5 | |
| | 73-26 | 20 | 55925/7570 | 5.8 | |
| | 73-26 | 50 | 22055/40937 | 7.0 | |
| Nov. 22, 1991, Dec. 10, 1991 | B3-A1/7 | | 3250/4087 | | |
| | 73-26 | 1 | 15277 | 4.7 | |
| | 73-26 | 20 | 41898 | 12.9 | |
| | 73-26 | 50 | 96941 | 29.8 | |
| Apr. 26, 1992 | B3-A1/7 | | 4692 | | |
| | 73-26 | 1 | 22934/26340 | 5.2 | |
| | 73-26 | 20 | 24935/17237 | 4.5 | |
| | 73-26 | 50 | 47088/78462 | 13.4 | |

ND = Not Determined

The data in Table 1 show the increased expression levels of α-amidating enzyme in this cell line as compared to that of the previously developed B3/A1-7 cell line. Co-amplification of α-amidating enzyme gene and the dhfr gene is apparent by the cell line's ability to express more enzyme with continued subculture at increased concentrations of methotrexate. The cells grown in the presence of 20 μM or 50 μM methotrexate had the best expression levels after 3-4 months of selective amplification. When continuously subcultured for several months, the expression levels of α-amidating enzyme decreased. Early frozen stocks of this cell line were therefore used for prepared suspension adapted cell lines.

Characterization of a Suspension Adapted α-Amidating Enzyme Expressing Cell Line 73-26

The ultimate goal in developing this cell line was to develop a process that was stable without the selective pressure of methotrexate and G418. Another desired attribute of the cell line was that it should be grown to relatively high cell densities in a suspension culture. The method used to achieve those goals is described below.

Preparation of Suspension Adapted, Selection-Free Cell Lines

Preparation of selection-free suspension adapted cells required that UGL 73-26 adherent cells be weaned off of serum, methotrexate and G418. A multi prong attack, FIG. 5, was developed to accomplish this task; a matrix of removal was established with the ultimate goal of adding the least number of cell doubling on the final cell line as possible. An early freeze, Dec. 16, 1991, of the 73-26 20 μM methotrexate cell line was thawed to establish a suspension adapted, serum free, selection free cell line for future developmental studies. Although the PAM activity in 50 μM methotrexate was somewhat higher attempts to re-establish an actively growing 73-26 50 μM cell line were unsuccessful. The α-amidating enzyme productivity of the cell line was assessed prior to initiating the suspension adaptation protocol, Table 2.

TABLE 2

Productivity of 73-26 20 μM

| Cell line | α-AE (U/$10^6$ cells/Day) |
|---|---|
| CHO K1 | 0 |
| B3/A1-7 | 22,555 |
| 73-26 | 446,625 |

The PAM activity of this cell line prior to adapting it to suspension culture had 20-fold greater activity on a per cell basis than the B3/A1-7 control. The enzyme activity for both the control cell line and 73-26 were 5-10 times that observed in the original testing just prior to when the cell line was frozen, Dec. 16, 1991 (Table 1).

Figure 6:
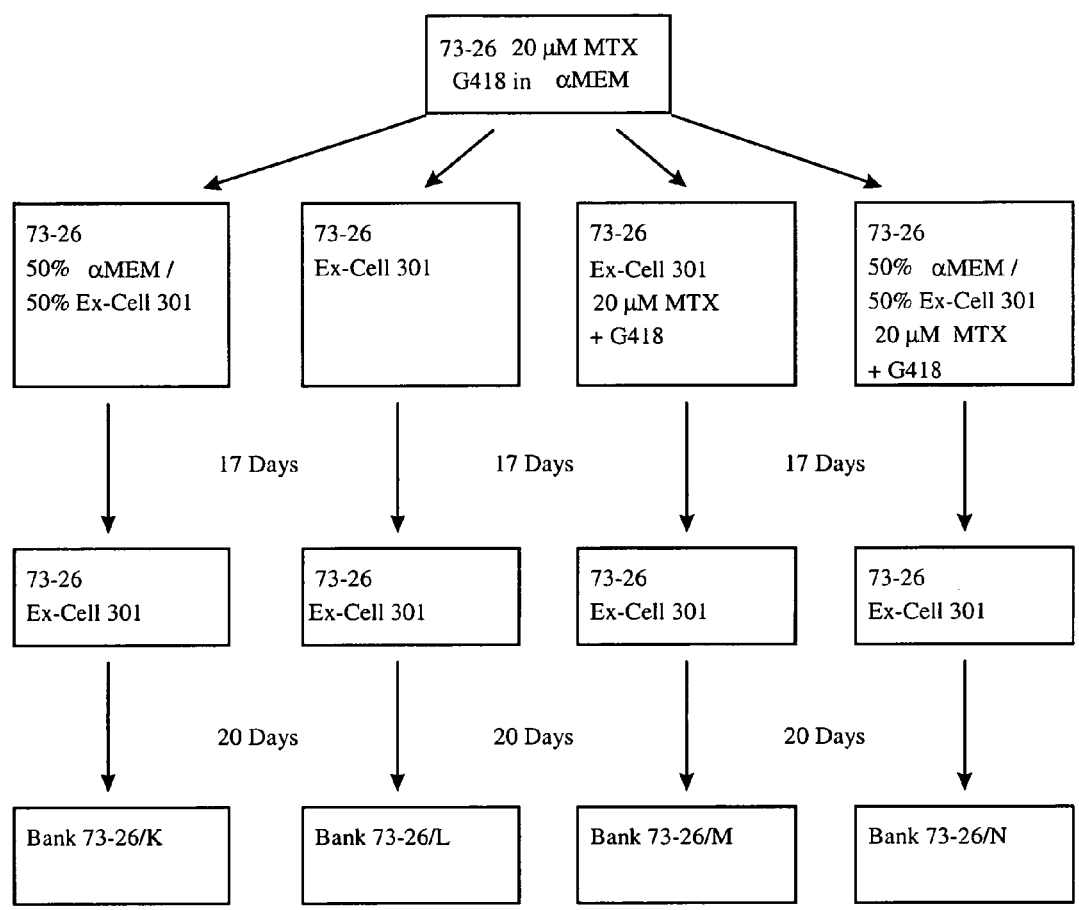
FIG. 6 is a 73-26 suspension adaptation scheme.

Four new suspension adapted, serum free cell lines were generated as shown in FIG. 6. The cell lines, designated as 73-26/K-N were cryopreserved following a 37 day process.

α-Amidating Enzyme Production of Suspension Adapted 73-26

Banked cells from the new 73-26 cell lines (73-26/K, 73-26/L, 73-26/M, 73-26/N) were thawed and grown in spinner flasks. The cell lines were maintained by passaging the cells three times per week in Ex-Cell 301 media. At periodic intervals a complete medium exchange was done and a 24 h assessment of enzyme productivity evaluated by the α-AE assay. The cell lines were maintained for up to 80 days in culture. The semi-continuous batch process for the previous cell line, B3/A1-7, was a 40-day process and we chose to evaluate the cell line production stability at twice the length of this procedure. The data from this study are shown in Table 3. During the course of this study cell line 73-26/L was terminated between day 22 and day 40, all other cell lines were actively growing at the end of the 80-day period.

TABLE 3

Enzyme Productivity of Suspension Adapted Cell Lines 73-26/K-N

| Cell line | Days in Culture | α-AE Activity (U/$10^6$ cells/Day) | Actual or Mean α-AE (U/$10^6$ cells/Day) | Relative Activity to B3/A1-7* |
|---|---|---|---|---|
| B3/A1-7 | 15 | 4907 | 5068 | |
| | 15 | 5778 | | |
| | 17 | 4520 | | |
| | 42 | 15697 | 15697 | |
| | 60 | 3773 | 3820 | |
| | 60 | 3867 | | |
| | 70 | 12677 | 12677 | |
| | 80 | 14246 | 14246 | |
| 73-26/K | 20 | 16872 | 11836 | 2.34 |
| | 20 | 10778 | | |
| | 22 | 7859 | | |
| | 40 | 8274 | 11609 | 0.74 |
| | 47 | 14944 | | |
| | 60 | 8616 | 5827.5 | 1.53 |
| | 60 | 3039 | | |
| | 70 | 10790 | 10790 | 0.85 |
| | 80 | 1933 | 1933 | 0.14 |
| 73-26/L | 20 | 10163 | 8731 | 1.72 |
| | 20 | 7076 | | |
| | 22 | 8955 | | |
| 73-26/M | 20 | 14728 | 9954 | 1.97 |
| | 20 | 8910 | | |
| | 22 | 6223 | | |
| | 40 | 44882 | 36391 | 2.32 |
| | 47 | 27900 | | |
| | 60 | 24844 | 23580 | 6.17 |
| | 60 | 22316 | | |
| | 70 | 46457 | 46457 | 3.66 |
| | 80 | 41246 | 41246 | 2.90 |
| 73-26/N | 20 | 10173 | 13686 | 2.70 |
| | 20 | 15852 | | |
| | 22 | 15033 | | |
| | 40 | 27368 | 26243 | 1.67 |
| | 47 | 25117 | | |
| | 60 | 16175 | 22123 | 5.79 |
| | 60 | 28071 | | |
| | 70 | 39082 | 39082 | 3.08 |
| | 80 | 6915 | 6915 | 0.49 |

*Note: Days in culture testing periods compared are results from 15-22, 40-47, 60, 70 and 80.

Although all cell lines expressed significantly more α-amidating enzyme than B3/A1-7 at the early intervals, <40 days, only 73-26/M and 73-26/N were still producing large quantities of enzyme after 70 days. UGL 73-26/M was chosen for further development because it consistently produced more α-amidating enzyme over a 80 day period. The other three cell lines either stopped growing before the end of the 80 day test period or their productivity/cell/day waned over the last 20 days.

PreBanking, Cell Banking Characterization Studies of CHO K1, UGL 73-26, UGL 73-26/M MCB and UGL 73-26/M MWCB00

Characterization studies were performed on the host cell line (CHO K1), a progenitor cell line (73-26) and the UGL 73-26/M seed bank. The 40 vial UGL 73-26/M seed bank was prepared on Feb. 4, 1998. Each vial of the seed bank contains $4 \times 10^6$ cells/mL in 90% Ex-Cell 301/10% DMSO. All studies performed were evaluated as consistent with the results required of a CHO cell line to be made into a MCB and MWCB, see Table 4.

The Master cell bank UGL73-26/M cell line was made at BioReliance Corp. Several of the 118 MCB vials were used for a full characterization of the cell line. Results from all studies of the UGL 73-26/M MCB are consistent with a cell line of CHO origin and negative for infectious agents. A vial of the UGL 73-26/M MCB was used to create a 238 vial manufacturer's working cell bank, UGL 73-26/M MWCB00, at BioReliance Corp. All results from studies of the UGL 73-26/M MWCB00 are consistent with cell line of CHO origin and negative for infectious agents.

TABLE 4

Summary of CHO Cell Characterization Studies

| Cell Banking Phase | Test Article | Test | Results | Lab Completion Date | Report # |
|---|---|---|---|---|---|
| PreBanking | CHO K1 | Transmission Electron Microscopy | Negative - No cells with A-type and budding C-type particles | Aug. 23, 1999 | AA18UW.013000.PAI |
| | UGL 73-26 | Transmission Electron Microscopy | Negative - No cells with A-type and budding C-type particles | Aug. 17, 1999 | AA18PK.013000.PAI |
| | UGL 73-26/M Seed Bank | Sterility | Satisfactory | Feb. 17, 1999 | AA11VS.510000.BSV |
| | | Mycoplasma | Negative | Mar. 02, 1999 | AA11VS.102003.BSV |
| | | MVM - PCR Assay | Negative | Feb. 09, 1999 | AA11VS.105026.BSV |
| | | Transmission Electron Microscopy | Negative - 3 cells with A-type and budding C-type particles | Mar. 05, 1999 | AA11VS.013000.PAI |
| | | Murine Retrovirus - Co-Cultivation with Mink Lung Cells | Negative | Sep. 14, 1999 | AA18UH.011001.BSV |
| | | Repeat of Transmission Electron Microscopy | Negative - No cells with A-type and budding C-type particles | Sep. 15, 1999 | AA18UH.013000.PAI |
| Master Cell Bank | UGL 73-26/M MCB | Sterility | Satisfactory | Dec. 21, 1999 | AA24KX.510000.BSV |
| | | Mycoplasma | Negative | Jan. 03, 2000 | AA24KX.102003.BSV |

TABLE 4-continued

Summary of CHO Cell Characterization Studies

| Cell Banking Phase | Test Article | Test | Results | Lab Completion Date | Report # |
|---|---|---|---|---|---|
| | | Isozyme | Consistent with Chinese hamster origin | Feb. 09, 2000 | AA24KE.380001.BSV |
| | | InVitro adventitious agents | Negative | Feb. 09, 2000 | AA24KE.003000.BSV |
| | | InVivo Inapparent Viruses | Negative | Feb. 11, 2000 | AA24KE.005002.BSV |
| | | InVivo adventitious agents | Negative | Feb. 15, 2000 | AA24KE.004005.BSV |
| | | Transmission Electron Microscopy | Negative - No cells with A-type and budding C-type particles | Feb. 08, 2000 | AA24KE.013000.PAI |
| | | Reverse Transcriptase | Non-informative | Jan. 15, 2000 | AA24KE.002000.BSV |
| | | Murine Retrovirus - Co-Cultivation with Mink Lung Cells | Negative | Feb. 01, 2000 | AA24KE.011001.BSV |
| | | Murine Retrovirus - Co-Cultivation with RD Cells | Negative | Feb. 01, 2000 | AA24KE.011002.BSV |
| | | MVM - PCR Assay | Negative | Feb. 03, 2000 | AA24KE.105026.BSV |
| | | MAP | Negative | Feb. 25, 2000 | AA24KE.004000.BSV |
| | | InVitro Bovine Virus | Negative | Feb. 04, 2000 | AA24KE.032004.BSV |
| | | InVitro Porcine Parvovirus | Negative | Feb. 04, 2000 | AA24KE.033004.BSV |
| Manufacturer's Working Cell Bank | UGL 73-26/M MWCB00 | Sterility | Satisfactory | Mar. 24, 2000 | AA27LH.510000.BSV |
| | | Mycoplasma | Negative | Apr. 07, 2000 | AA27LH.102003.BSV |
| | | InVitro adventitious agents | Negative | Apr. 26, 2000 | AA27LH.003031.BSV |
| | | InVivo Inapparent Viruses | Negative | May 16, 2000 | AA27LH.005002.BSV |
| | | Isozyme | Consistent with Chinese hamster origin | Apr. 21, 2000 | AA27LH.380001.BSV |

Process Development Studies of UGL 73-26/M in Spinner Flasks and Stirred Tank Bioreactors Since preliminary experiments had indicated that the productivity of the cell line could not be maintained consistently over a large number of generations, a batch fermentation protocol was investigated. A batch protocol also offers the advantages of ease of scheduling, easier scalability and less drastic consequences of batch failure. Fermentation process development for UGL 73-26/M required investigation of a number of parameters that could influence the cellular productivity of the cell line. The fermentation development detailed below shows pivotal studies investigating dissolved oxygen (DO), pH and media supplementation. Fermentation parameters not studied were impeller RPM and fermentation temperature.

Effect of Dissolved Oxygen on α-Amidating Enzyme Expression

Figure 7:
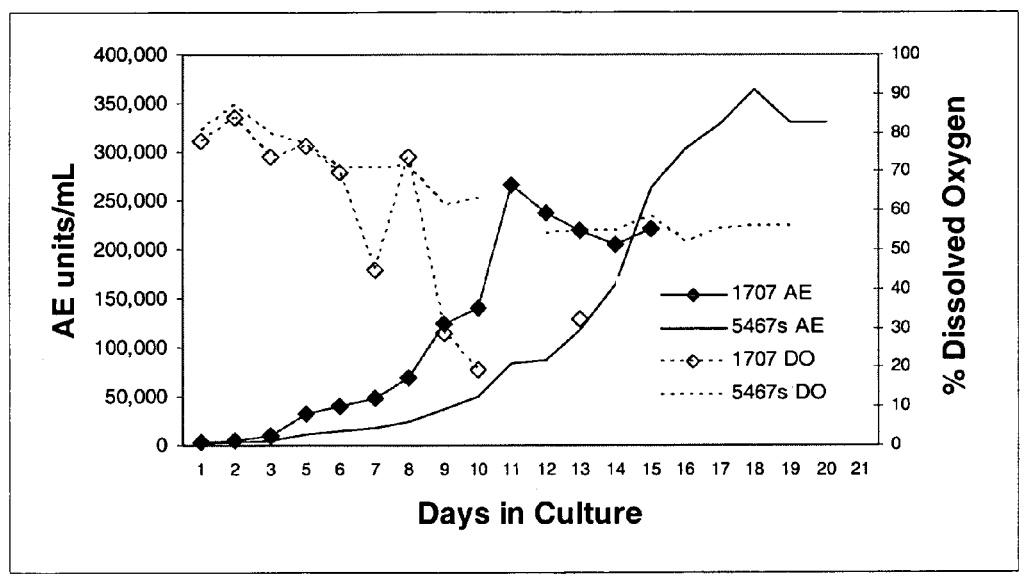
FIG. 7 is a dissolved oxygen concentration and α-AE productivity in spinner flasks.

An experiment was performed to examine the effect of dissolved oxygen concentration of the CHO culture media in a spinner flask. Spinner flasks were seeded with $0.1 \times 10^6$ cells/mL. Two spinner flasks contained 150 mL of media in a 250 mL Techne spinner flask, whereas the third spinner flask contained 250 mL of media. Daily measurements of dissolved oxygen were taken on all spinner flasks. Aliquots of clarified conditioned media were taken daily for assessment of α-AE productivity by the α-AE assay. Two culture media were used in this study, a low protein CHO media (C1707, Sigma-Aldrich) and a protein-free CHO media (C5467, Sigma-Aldrich). The direct comparison of UGL 73-26/M grown in the two media is shown in FIG. 7. The dissolved oxygen level in the two cultures was markedly different. The cells grown in 150 mL of C1707 produced less total enzyme/mL than those cells grown in an equivalent volume of C5467 culture media. Although the initial dissolved oxygen concentration of the media were the same, ~80% DO, the dissolved oxygen concentration of the C5467 media culture never went below 50%. The DO content of the C1707 culture was less than 50% by Day 9 and the peak activity of the culture was two days later. These data indicate that there may be a correlation between DO content/cell viability/α-AE productivity.

Spinner volume was also investigated as a potential critical parameter. Because the spinner flask is not maintained at a constant dissolved oxygen concentration, the culture's ability to maintain dissolved oxygen is relative to the cultures surface:volume ratio. Increasing the culture volume of a spinner appreciably alters the surface:volume ratio. Identical cultures were started except that the culture volume in one spinner was 150 mL (5467s) and the other was 250 mL (5467sa). The effect of changes in surface:volume ratio on % DO and α-AE productivity are shown in FIG. 8.

Figure 8:
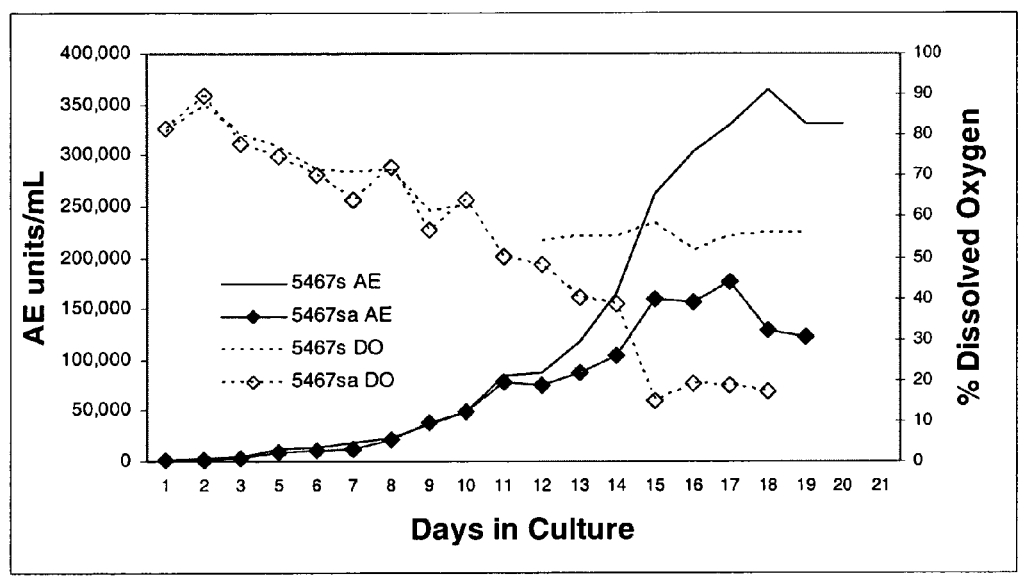
FIG. 8 is an effect of spinner volume on DO and α-AE productivity.

The data shown in FIG. 8 show that the productivity of the culture is greatly affected by the dissolved $O_2$. Whether the dissolved $O_2$ concentration decreases because of the utilization by the culture or because of the effect from differences in surface:volume ratio; when the DO concentration is less than 50% the culture ceases to express more α-amidating enzyme within 48-72 h. The dissolved $O_2$ in the bioreactor should be maintained at 70% to reflect the dissolved oxygen concentration during the phase of the culture where the cells are the most healthy and productive.

Effect of Media on α-Amidating Enzyme Expression

As parts of studies either designed to facilitate selection of the most appropriate choice of growth medium for UGL 73-26/M or while defining bioreactor growth conditions numerous spinner cultures were initiated with two CHO culture media, C1707 and C5467 (Sigma-Aldrich). Both culture media are defined, C1707 is a low protein media with transferrin added to the media and C5467 is a non-animal protein media. Both media, when purchased, required addition of L-glutamine to a final concentration of 2 mM. Table 5 below tabulates the data from a large sampling of spinner flasks with either of the two media.

TABLE 5

Summary Of Spinner Cultures Data With C1707 And C5467 CHO Culture Media.

| Media Formulation | n = | | Peak Enzyme Activity (units/mL) | Day of Peak Activity | Peak Cell Density ($10^6$ cells/mL) | Day of Peak Cell Density |
|---|---|---|---|---|---|---|
| C5467 | 21 | Mean | 363,366 | 15 | 1.48 | 11 |
|  |  | SEM | 51,708 | 0.5 | 0.11 | 0.6 |
| C1707 | 12 | Mean | 322,691 | 14 | 1.92 | 10 |
|  |  | SEM | 86,045 | 2.9 | 0.66 | 3.0 |

The data in Table 5 show no substantial difference in enzyme productivity of UGL 73-26/M cell line in either media. Sigma CHO culture media, C5467, may be more regulatory compliant media choice concerning future regulatory guidelines in both the US and the European Union because it contains no animal sourced media components. Sigma CHO culture media, C5467, is the media of choice for future studies.

Effect of Glucose on α-Amidating Enzyme Expression

Studies investigating the nutrient status of a UGL73-26/M batch culture revealed that 4-5 days after the initiation of the culture the glucose concentration in the media was approximately 50% (2 g/L) that of virgin media. A thorough study of the effect of glucose supplementation on enzyme productivity was undertaken as a series of spinner flask experiments where additional glucose is added to the culture. Spinner flasks were supplemented with 2 g/L glucose 1 to 3 times at specific time intervals. The effect of glucose addition on α-AE productivity is shown in Table 6.

TABLE 6

Glucose Supplementation - Relative Enzyme Expression
Peak Activity - % of Control

| Day of Glucose Addition | 00108 | 00110 | 2130-D-1001 Fairfield | 2131-D-1001 | 2131-D-1002 | Average |
|---|---|---|---|---|---|---|
| None | 100 | 100 | 100 | 100 | 100 | — |
| 5 | 151 |  | 160 |  |  | 156 |
| 5, 10 | 235 | 162 | 144 | 111 | 65 | 143 |
| 5, 10, 15 | 197 |  | 192 |  |  | 195 |
| 8, 15 | 179 |  | 149 |  |  | 164 |

TABLE 7

Glucose Supplementation - Day Of Peak Enzyme Expression
Day of Peak Activity

| Day of Glucose Addition | 00108 | 00110 | 2130-D-1001 Fairfield | 2131-D-1001 | 2131-D-1002 | Average |
|---|---|---|---|---|---|---|
| None | 15 | 13 | 12 | 13 | 13 | 13 |
| 5 | 17 |  |  |  |  | 17 |
| 5, 10 | 19 | 19 | 13 | 23 | 17 | 18 |
| 5, 10, 15 | 19 |  | 15 |  |  | 17 |
| 8, 15 | 19 |  | 16 |  |  | 18 |

Addition of glucose to a batch culture of UGL 73-26/M increased the maximum productivity of the culture by 50-100% depending on the glucose addition regimen. The spinner flasks that were supplemented with glucose on days 5, 10 and 15 appear to express the most enzyme as compared to non-supplemented controls. The average relative productivity of these cultures was 195% of control. Other supplemented cultures were only slightly less productive (143-164%) than those supplemented three times. All cultures that were supplemented with additional glucose showed delayed peak enzyme concentrations in the media. Peak enzyme concentrations were observed on days 17/18 for glucose supplemented cultures versus day 13 in the control non-supplemented cultures, Table 7.

Effect of pH on α-Amidating Enzyme Expression

Figure 9:
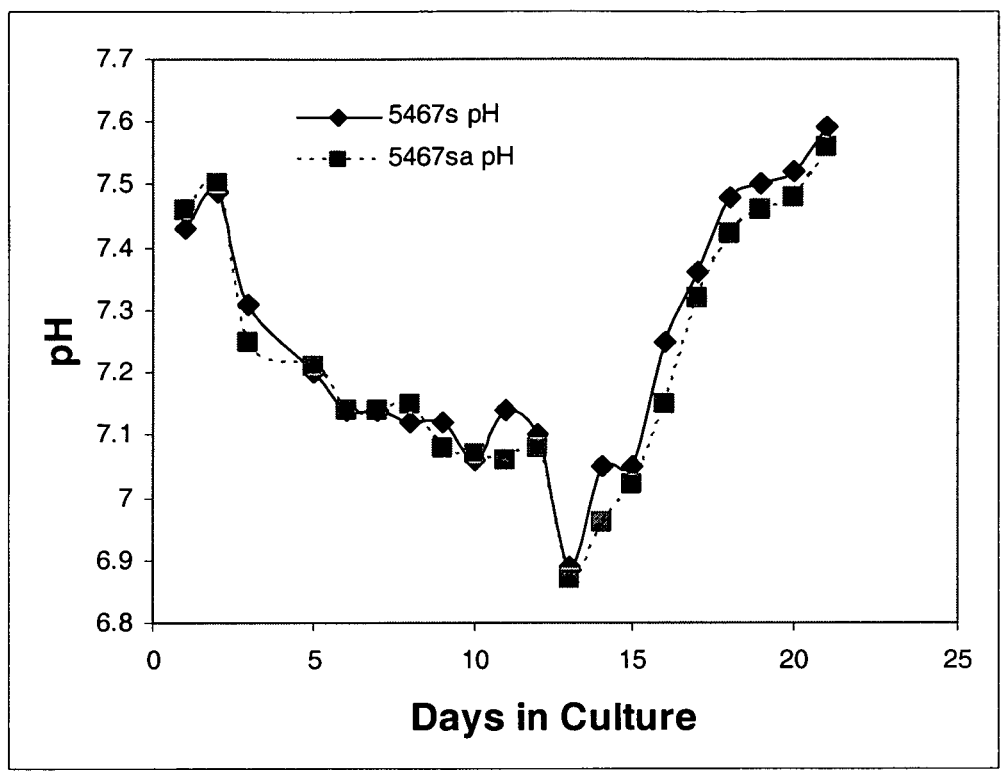
FIG. 9 is a spinner culture pH of UGL 73-26/M.

The pH of the conditioned media one of the process variables that can be controlled in a stirred tank bioreactor which can not be addressed in a spinner flask. In a spinner flask, the pH of the culture is allowed to drop as the media components are consumed and as cellular byproducts are produced. The pH profile of two 250 mL spinner flasks of UGL 73-26/M containing either 150 mL (5467s) or 250 mL (5467sa) are shown below in FIG. 9. The pH of the culture decreased during the first portion of the batch and then rose during the last portion of the culture. The decrease in pH is likely due to increased lactate concentration in the culture at the beginning of the culture. The rise in the pH at the end of the culture, is due to the cells catabolizing the lactate as a carbon source. The productivity of the culture is unaffected by the decrease in pH (FIG. 8).

Figure 10:
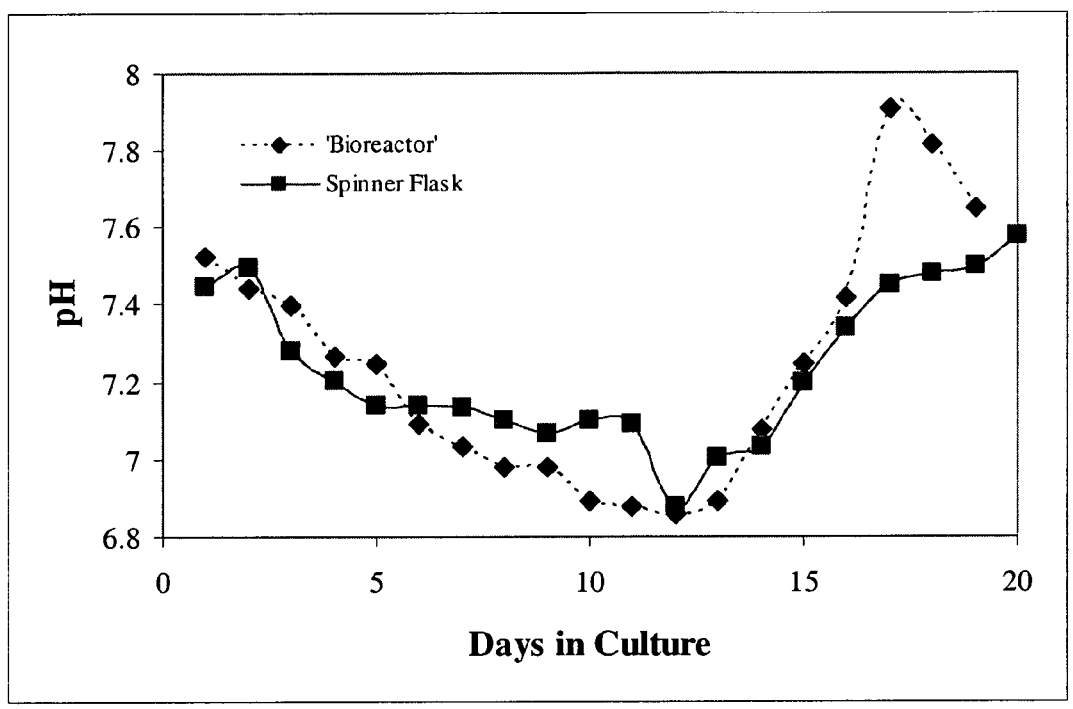
FIG. 10 is a pH profile of stirred tank bioreactors and spinner flasks without pH control.

Several (n=5) 6-10 L stirred tank bioreactors were run without pH control to mimic conditions in a spinner flask. CHO cells in the stirred tank bioreactors were grown in C5467 media, at 70% DO and at 37° C. The average pH profile of the conditioned media in the bioreactor is similar to that observed in the two spinner flasks, FIG. 10. The dissolved oxygen concentration in the bioreactor was maintained at 70% and the temperature at 37° C.

In addition to the bioreactor runs described above without pH control, a series of bioreactors were run where the pH of the reactor was allowed to free fall to the set pH point (between 7.0-7.4). At the time that the desired pH was reached, it was maintained at that pH for the duration of the fermentation. CHO cells in the stirred tank bioreactors were grown in C5467 media, at 70% DO and 37° C. The effect of maintenance of pH control on α-AE productivity in a stirred tank bioreactor is shown in FIG. 11.

Figure 11:
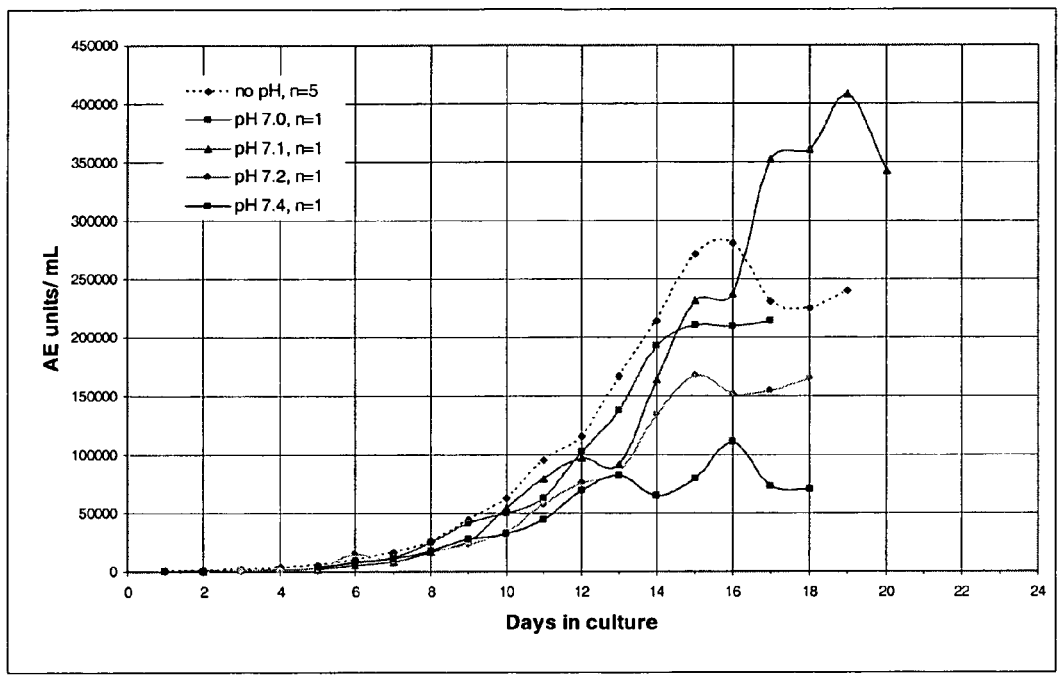
FIG. 11 is a pH effect on UGL 73-26/M α-AE productivity in stirred tank bioreactors.

FIG. 11 shows the average α-AE activity in the bioreactor for each day throughout the run for those runs when a pH set point was not initiated. The data from individual runs when the pH set point was set only after the pH was within 0.5 pH units of the set point are also shown in FIG. 11. There is a clear correlation between culture pH and enzyme activity. The activity profile for the bioreactor run with no pH set point is superior for all runs during the initial 16 days of culture. The lone exception was the profile for the run where the pH set point was 7.1. The difference was probably because that culture lasted longer than the other runs. Peak α-AE activity for the average no pH set point studies was 280,707 units/mL on day 16.

There was no effect of pH on viable cell density (data not shown). The cultures grew to a peak viable cell density of $1.0\text{-}1.5 \times 10^6$ cells per mL. Maximum cell density was reached 8 to 10 days after the bioreactor was inoculated. There was no effect of pH on cell viability except for the one culture run at pH 7.1 (data not shown). Cell culture viability was greater than 50% viable for 15 or more days in culture. The one bioreactor that was run with a pH set point of 7.1 maintained >50% viable cells for 20 days in culture.

Summary of Research and Development Fermentation Parameters for UGL 73-26/M

Following the establishment of the α-AE expressing cell line UGL 73-26/M, a series of experiments were done to define critical parameters for optimal expression of the α-amidating enzyme. It was determined that an animal protein-free media (Sigma, C5467) supported high levels of expression of the enzyme. The CHO cells could be grown as a batch culture in C5467 media supplemented with L-glutamine at a final concentration of 2 mM. However, the culture requires D-glucose supplementation to further boost the productivity of the culture. Optimum glucose supplementation was 2 g/L on days 5, 10 and 15. The DO concentration of the bioreactor should be maintained at 70% and the pH of the bioreactor allowed to adjust to the pH that is a function of the buffering capacity of the media and the metabolism of the media components by the CHO cells.

Downstream Purification Development UGL 73-26/M

The following section summarizes our downstream purification development for PAM produced using the UGL 73-26/M clone. Only representative experiments, which provide a logical progression of the process development work, are included in the summary. A brief description of each step is provided that describes the function of that step in the purification process. Purification runs were analyzed using SDS-PAGE (constant protein and constant units), PAM activity assay and Bradford protein assay. All of the experiments were completed prior to or shortly after the technology transfer to the Boonton, N.J. pilot facility. The methods described herein were used to manufacture PAM batches 1330-D-1003, 1330-D-1004, 1330-D-1005, 1330-D-1006, 1330-1009 and 1330-1010.

Tangential Flow Filtration No. 1 (TFF 1)

Step Description: The TFF 1 step is utilized to concentrate and diafilter the conditioned CHO cell media prior to chromatography. The conditioned media is concentrated and the conductivity is decreased by diafiltration to facilitate binding to the anion exchange column. The TFF 1 step employs a Pellicon 2 Module fitted with a regenerated cellulose PLCTK 30 kDa membrane (Millipore).

Research and Development: The initial investigation of this step focused on whether or not TFF would be necessary prior to chromatography. Reducing the conductivity of the conditioned CHO media by dilution with water was investigated as an alternative to TFF. Failure to dilute the conditioned media prior to chromatography caused a large portion of the PAM activity to reside in the flow through following loading. Decreasing the conductivity of the conditioned media to approximately 5 mS minimized the amount of PAM activity detected in the flow through. However, two problems were identified when the conditioned media was loaded directly onto the anion exchange column. One of the medium components irreversibly bound to the column and caused severe discoloration of the resin. Another medium component that exhibited enormous UV absorbance characteristics co-eluted with the PAM activity following gradient elution.

Conditioned CHO cell medium (C5467) was diluted with water to reduce the conductivity to approximately 5 mS and loaded directly onto a Q-Sepharose FF column (Pharmacia) equilibrated with 50 mM TRIS, 120 mM NaCl, 0.001% TX-100 pH 8.0. The column was subjected to a linear gradient from 100% A (50 mM TRIS, 120 mM NaCl, 0.001% TX-100 pH 8.0) to 68% B (50 mM TRIS, 475 mM NaCl, 0.001% TX-100 pH 8.0) over 60 minutes. A large dark colored band appeared at the top of the column immediately following loading and remained throughout the chromatography run. The column was cleaned with 2 M NaCl and sanitized with 1.0 M NaOH. The cleaning and sanitization procedures failed to remove the dark band from the column. Subsequently, the column was subjected to a more stringent cleaning procedure. The column was subjected to the following series of cleaning reagents: 0.5 M NaOH 1 M NaCl, 0.1 M acetic acid, 0.1 M acetic acid 1 M NaCl and 70% ethanol. None of the conditions tested were able to remove the dark band from the column (NEG:001:225-245). The colored band was identified as aurintricarboxylic acid, a component present in virgin C5467 medium. A 6 mg/L solution (media concentration) of aurintricarboxylic acid buffered to pH 8.0 with TRIS was loaded directly onto a Q-Sepharose FF column equilibrated with 50 mM TRIS, 120 mM NaCl, 0.001% TX-100 pH 8.0. The colored band appeared at the top of the column immediately following loading. The column was subjected to the same gradient elution and cleaning procedure described above. The aurintricarboxylic acid remained bound to the anion exchange column throughout the run (NEG:001: 276-290). The aurintricarboxylic acid readily polymerizes in aqueous solutions resulting in a macromolecule with a high charge density at pH 8.0. The negatively charged macromolecule apparently binds irreversibly to the anion exchange column much like DNA. Repeated applications of this material to the column are likely to decrease the loading capacity, and therefore will, negatively impact the overall column lifetime.

The second medium component was found to co-elute with the PAM. Unconditioned or virgin medium was loaded directly onto the Q-Sepharose FF column that was equilibrated with 50 mM TRIS, 120 mM NaCl, 0.001% TX-100 pH 8.0. The column was again subjected to the same gradient elution conditions described above. A large UV peak in the region where the enzyme typically elutes was observed (NEG:001:248-257). SDS-PAGE analysis of the peak purified from conditioned medium revealed that the material was either low molecular weight proteins or a non-proteinaceous medium component (NEG:001:225-245). The C5467 media contains protein hydrolysates that may account for the large UV peak that is coincident with the enzyme peak. Both medium components, the aurintricarboxylic acid and the unidentified UV peak, are effectively removed prior to chromatography by TFF. The enzyme is retained (retentate) by the 30 kDa membrane and the low molecular weight media components pass through the filter (permeate).

Conditioned medium was concentrated 10-fold and diafiltered using a Pellicon XL device fitted with a regenerated cellulose PLCTK 30 kDa membrane (Millipore). The material was diafiltered with 4-5 volumes of 25 mM TRIS, 0.0005% TX-100 pH 7.0 to a final conductivity of approximately 3 mS. The material was loaded onto a Q-Sepharose FF column equilibrated with 50 mM TRIS, 120 mM NaCl, 0.001% TX-100 pH 8.0. The column was subjected to gradient elution as described above. No discoloration of the resin was observed and the large UV peak that co-eluted with the enzyme was absent. The % recovery and specific activity of the resultant enzyme peak were determined to be 47% and $2.1 \times 10^6$ U/mg, respectively (NEG:004:263-283).

Enzyme stability at various stages of the TFF step was investigated. Conditioned medium was initially diafiltered with 50 mM TRIS, 0.001% TX-100 pH 7.0 followed by a 5-fold concentration. Samples of the diafiltration and concentration outputs were analyzed for loss of activity and degradation. No degradation was observed by SDS-PAGE and approximately 95% of the enzyme activity was recovered (NEG:008:245-251).

Anion Exchange Chromatography (Q-Sepharose FF)

Step Description: The anion exchange (AEX) chromatography step provides a gross purification of the PAM from the conditioned CHO cell media. The step mainly removes higher molecular weight proteins. However, some low molecular weight proteins are also removed, including truncated forms of the enzyme. The chromatography step routinely affords a 2 to 3-fold purification of the enzyme. The % recovery of active enzyme is typically 50-75%. DNA that may be present in the feed stream following fermentation of the CHO cells is effectively removed at this stage of the process.

Research and Development: Prior to development of the Q-Sepharose FF step, we briefly investigated purification of PAM using cation exchange (CEX) chromatography. The use of CEX chromatography was investigated with and without the initial TFF step. Purification was carried out on a SP550C (TosoHaas) column employing mobile phases at pH 5.0-6.0. In each case, poor resolution and recovery resulted; much of the enzyme activity was identified in the flow through following loading (NEG:004:006-029 and NEG:004:102-119). Decreasing the pH of the mobile phases to facilitate binding was not considered due to the potential lack of stability of the enzyme at low pH. At this point, CEX chromatography was abandoned.

A series of AEX chromatography runs employing gradient elution was investigated on a Q-Sepharose FF column. All Q-Sepharose FF purifications were carried out on a (1.1×13.7 cm) column operated at 180 cm/hr. Early in the purification development, the availability of fresh conditioned medium was limited; therefore many of these experiments were performed with freeze/thaw material. Conditioned medium was concentrated/diafiltered by TFF and applied to the column equilibrated with 50 mM TRIS, 120 mM NaCl, 0.001% TX-100 pH 8.0. The column was subjected to a linear salt gradient from 100% A (50 mM TRIS, 120 mM NaCl, 0.001% TX-100 pH 8.0) to 68% B (50 mM TRIS, 475 mM NaCl, 0.001% TX-100 pH 8.0) over 60 minutes. Similar gradient runs employing HEPES buffers at either pH 7.0 or pH 8.5 were also investigated. Generally, the gradient runs afforded little purification and resulted in poor enzyme specific activity (NEG:004-139-156, NEG:005:119-132, NEG:009:009-022 and NEG:009:024-038). In many instances the enzyme activity was spread out throughout the gradient, perhaps as a result of differential glycosylation.

As the development continued, step elution methods using sequential salt steps were investigated on the Q-Sepharose FF column. Concentrated/diafiltered conditioned media was loaded onto a Q-Sepharose column equilibrated with 50 mM TRIS, 120 mM NaCl, 0.001% TX-100 pH 8.0. The column was subjected to sequential step elution with 175 mM NaCl, 225 mM NaCl and 275 mM NaCl. The enzyme activity was distributed equally between the 175 mM and 225 mM salt steps, with an overall % recovery of approximately 41%. Analysis by SDS-PAGE revealed the presence of 75 kDa enzyme in both the 175 mM and the 225 mM NaCl fractions (NEG:005:198-211). Enzyme activity in both salt steps may be due to differences in glycosylation or perhaps truncated forms of the enzyme that retain activity.

Fresh conditioned medium from either spinner flasks or 10 L bioreactor runs was used for the remainder of the anion exchange experiments. Conditioned CHO medium from spinner flask 00020S3 was subjected to TFF and then loaded onto the Q-Sepharose FF equilibrated with 50 mM TRIS, 120 mM NaCl, 0.001% TX-100 pH 8.0. The enzyme was eluted from the column with a single salt step, 50 mM TRIS, 225 mM NaCl, 0.001% TX-100 pH 8.0. The % recovery and specific activity values of the collected peak were 34% and $1.9 \times 10^6$ U/mg, respectively (NEG:008:021-033). Similarly, conditioned CHO medium from a 10 L bioreactor (00021BR, day 14) was subjected to TFF and purification on the Q-Sepharose using a single 225 mM NaCl step. The % recovery and specific activity values for this run were 37% and $2.3 \times 10^6$ U/mg, respectively (NEG:008:065-075).

Step elution using HEPES mobile phases was also investigated in an effort to improve the recovery of active enzyme. Duplicate purification runs employing 50 mM HEPES, 225 mM NaCl, 0.001% TX-100 pH 8.0 as the elution buffer were performed. Conditioned CHO media from a 10 L bioreactor run (Boonton Pilot Facility, run No. 1 day 15) was used as the input material for these purification runs. The % recovery and specific activity for both purification runs were approximately 60% and $3.0 \times 10^6$ U/mg, respectively (NEG:008:263-288). The use of HEPES mobile phases apparently improved the % recovery and purity of the enzyme.

The effect of cell viability on the Q-Sepharose FF purification was investigated. Purification of conditioned CHO medium from a 10 L bioreactor run (B00101) harvested on day 14 and day 21 were compared. The cell viability on day 14 and day 21 was measured and determined to be 95% and 48%, respectively. Conditioned CHO medium from day 14 and day 21 were subjected to TFF and Q-Sepharose FF purification using 50 mM HEPES, 225 mM NaCl, 0.001% TX-100 pH 8.0 as the step elution buffer. Purification of the day 14 material resulted in a recovery of 49% and a specific activity of $2.15 \times 10^6$ U/mg, while the day 21 run afforded 40% recovery and $2.1 \times 10^6$ U/mg (NEG:009:114-125 and NEG:009:149-166). Purifications were also carried out using conditioned CHO medium from a 10 L bioreactor run (00107BR) on day 12 and day 15. The cell viability on day 12 and day 15 were measured and determined to be 86% and 80%, respectively. In each case, the enzyme was eluted from the Q-Sepharose FF column with 50 mM TRIS, 225 mM NaCl, 0.001% TX-100 pH 8.0. The day 12 material resulted in a 62% recovery and a specific activity of $1.9 \times 10^6$ U/mg, while the day 15 material gave a 54% recovery and a specific activity of $4.3 \times 10^6$ U/mg (NEG:009:195-203 and NEG:009:227-236). Cell viability did not appear to have a significant affect on the overall % recovery or specific activity of the enzyme following AEX chromatography.

Critical parameters for the Q-Sepharose FF chromatography were identified and investigated to establish working ranges. Scenarios designed to challenge the purification procedure were defined and investigated to determine the impact on the recovery and purity of the enzyme. Two Q-Sepharose FF purification runs were compared using different step elution buffers, either 50 mM TRIS, 250 mM NaCl, 0.001% TX-100 pH 7.8 or 50 mM TRIS, 200 mM NaCl, 0.001% TX-100 pH 8.2 (low pH/high salt and high pH/low salt). The rationale for these experiments was to subject the chromatography to extreme elution conditions in order to define the working ranges. TFF treated conditioned CHO medium from a 10 L bioreactor run (2132-D-1004) was used as the input for purifications. In the low pH/high salt scenario, the conditioned media was loaded onto the column equilibrated with 50 mM TRIS, 120 mM NaCl, 0.001% TX-100 pH 7.8. The enzyme was eluted from the column with 50 mM TRIS, 250 mM NaCl, 0.001% TX-100 pH 7.8. The % recovery and specific activity values of the enzyme were 66% and $2.0 \times 10^6$ U/mg, respectively (NEG:010:151-161). The conditioned medium in the high pH/low salt scenario was loaded onto the column equilibrated with 50 mM TRIS, 120 mM NaCl, 0.001% TX-100 pH 8.2 and eluted with 50 mM TRIS, 200 mM NaCl, 0.001% TX-100 pH 8.2. The % recovery and specific activity of the enzyme in this case were 66% and $2.4 \times 10^6$ U/mg, respectively (NEG:010:140-150). Based on these data, the Q-Sepharose FF column can be operated at a pH range of [7.8-8.2] and the concentration of sodium chloride in the elution buffer can vary between [200 mM-250 mM NaCl].

A working capacity for the Q-Sepharose FF column was established to assist in the purification scale-up for 30 L bioreactor runs. The working capacity of the column was defined in two ways: [units of enzyme/mL of resin] and [mg of protein/mL of resin]. Breakthrough for this experiment was defined as a total of ≥10% of the enzyme activity identified in the flow through and wash steps. Conditioned CHO medium (100 mL) that had been subjected to TFF (2132-D-1002) was loaded onto a Q-Sepharose FF column equilibrated with 50 mM TRIS, 120 mM NaCl, 0.001% TX-100 pH 8.0. The enzyme activity and protein concentration of the conditioned medium was determined to be $1.97 \times 10^6$ U/mL and 2.41 mg/mL, respectively. The AEX column (Millipore Vantage-L, 1.1×13.7 cm) was operated at a linear velocity of 180 cm/hr. Step elution was carried out with 50 mM TRIS, 225 mM NaCl, 0.001% TX-100 pH 8.0. Less than 1% of the total enzyme activity was identified in the column flow through and wash steps. Approximately 51% of the enzyme units were recovered in the main peak. Based on a column volume of 13.0 μL, the working capacity was calculated to be either [$1.51 \times 10^7$ U/mL of resin] or [18.5 mg of protein/mL resin] (NEG:010:081-092). Future experiments are planned to determine a true loading capacity of the Q-Sepharose FF step.

Hydrophobic Interaction Chromatography (Phenyl-Sepharose FF, Low Substitution)

Step Description: The Hydrophobic Interaction Chromatography (HIC) step removes the majority of the protein impurities remaining after the AEX step and provides an additional 2-fold purification. SDS-PAGE analyses following HIC revealed a single major band with a few minor lower molecular weight impurities. Typically, the % recovery of active enzyme following HIC is 50-75%.

Research and Development: The purification process developed for PAM produced from the B3/A1-7 clone also utilized HIC. Mobile phases containing ammonium sulfate were employed to promote ligand-protein interaction. Prolonged exposure of the enzyme to buffers containing ammonium sulfate resulted in unpredictable precipitation and enzyme denaturation. Other salts in the Hofineister series, such as sodium chloride and sodium citrate, were investigated in an attempt to minimize these problems.

Reverse linear gradients utilizing mobile phases containing sodium chloride were initially investigated. The input materials for these chromatography studies were either TFF 1 outputs or Q-Sepharose FF outputs. Direct HIC following the initial TFF step was investigated in an attempt to eliminate the AEX step. Typically, the enzyme was diluted with an equal volume of water followed by an equal volume of 20 mM TRIS, 4 M NaCl pH 7.0. Dilution with water prior to salt addition decreases the protein concentration minimizing the possibility of precipitation caused by "salting-out." The diluted material was loaded onto a Phenyl-Sepharose FF column equilibrated with 10 mM TRIS, 2.0 M NaCl pH 7.0. The enzyme was eluted from the column with a reverse linear gradient from 100% A (10 mM TRIS, 2.0 M NaCl pH 7.0) to 100% B (10 mM TRIS, pH 7.0) over 68 minutes. Generally, the % recovery of active enzyme was approximately 50% (NEG:005:170-185 and NEG:005:212-226).

Step elution methods employing the sodium chloride mobile phases were also investigated. Enzyme subjected to either TFF 1 or Q-Sepharose FF chromatography was diluted with an equal volume of water followed by an equal volume of 20 mM TRIS, 4 M NaCl pH 7.0. The diluted material was loaded onto an HIC column equilibrated with 10 mM TRIS, 2 M NaCl pH 7.0. The column was washed with additional equilibration buffer followed by a wash with 10 mM TRIS, 1.0 M NaCl pH 7.0. The enzyme was eluted from the column with 10 mM TRIS, 400 mM NaCl pH 7.0. The yield of active enzyme was fair but only marginal purification was achieved (NEG:008:034-046 and NEG:008:135-148). The use of sodium chloride did not appear to cause "salting out" as was the case with ammonium sulfate, however the enzyme was denatured over time in high concentrations of sodium chloride.

Sodium citrate was found to promote binding of the enzyme to the HIC column at relatively low concentrations. Conditioned CHO media subjected to TFF was diluted with an equal volume of water followed by an equal volume of 20 mM TRIS, 1.0 M sodium citrate pH 7.0 and loaded onto a Phenyl-Sepharose FF column equilibrated with 10 mM TRIS, 0.5 M sodium citrate pH 7.0. The column was washed with additional equilibration buffer and stripped with 10 mM TRIS, pH 7.0. No enzyme activity was identified in either the column flow through or wash fractions. Approximately 50% of the enzyme activity was identified in the 10 mM TRIS pH 7.0 fraction (NEG:005:064-076). This experiment was repeated using a lower final concentration of sodium citrate. At the lower salt concentration, the enzyme was diluted with an equal volume of water followed by an equal volume of 20 mM TRIS, 0.6 M sodium citrate pH 7.0 before loading onto the HIC column equilibrated with 10 mM TRIS, 300 mM sodium citrate pH 7.0. The column was washed with additional equilibration buffer and stripped with 10 mM TRIS pH 7.0. Results were essentially identical to the previous run; no activity was identified in either the flow through or wash fractions (NEG:008:203-213).

Gradient elution using the sodium citrate buffer system was investigated to assist in the development of a step elution method. A TFF output was diluted with an equal volume of water followed by an equal volume of 20 mM TRIS, 0.6 M sodium citrate pH 7.0 before loading onto the column equilibrated in 10 mM TRIS, 300 mM sodium citrate pH 7.0. The column was subjected to a reverse linear gradient from 100% A (10 mM TRIS, 300 mM sodium citrate pH 7.0) to 100% B (10 mM TRIS pH 7.0) over 70 minutes. A peak of enzyme activity was identified near the end of the gradient. Other protein impurities eluted in this area of the gradient as well and extended into the 10 mM TRIS pH 7.0 column strip (NEG:008:252-262). Step elution was examined to achieve better separation between the enzyme and the proteins that eluted in the 10 mM TRIS pH 7.0 strip.

The peak fraction (225 mM NaCl) from a Q-Sepharose FF purification (10 L bioreactor run, 00107BR, day 12) was diluted with an equal volume of water followed by an equal volume of 50 mM TRIS, 600 mM sodium citrate pH 7.0. The diluted material was loaded onto a Phenyl-Sepharose column equilibrated with 25 mM TRIS, 300 mM sodium citrate pH 7.0. The column was washed with additional equilibration buffer, followed by a second wash with 25 mM TRIS, 75 mM sodium citrate pH 7.0 and stripped with 25 mM TRIS pH 7.0. All of the enzyme activity was identified in the 75 mM sodium citrate fraction. The % recovery and specific activity were calculated to be 42% and $2.0 \times 10^6$ U/mg, respectively (NEG: 009:204-218). Better resolution between the enzyme and other protein impurities was achieved using this method.

HIC directly following TFF (no AEX step) was abandoned due to the ineffectiveness of the step to clear DNA from the crude feed stream. Four HIC purifications were performed using the sodium chloride step elution method detailed above. The input for these runs was B3/A1-7 conditioned CHO medium that had been subjected to TFF prior to chromatography. Our internal DNA specification at the time was <10 ng/mg protein. In each case, the level of residual DNA present in the main enzyme peak following HIC was found to be 6-10 times higher than the specification, thereby making the single step HIC purification unacceptable (NEG:006:137-159, NEG:006:176-187 and NEG:006:192-200).

A working capacity for the HIC purification step was investigated to assist in the 30 L scale-up effort. Breakthrough was defined as the presence of ≥10% of the enzyme activity in either the column flow through or the wash fractions. Q-Sepharose output (125 mL, 0.368 mg/mL, 710,563 U/mL) from production run 1330-D-1003 was diluted with an equal volume of water followed by an equal volume of 50 mM TRIS, 0.6 M sodium citrate pH 7.0. The diluted material was loaded onto a Phenyl-Sepharose FF column (Millipore Vantage-L, 1.1×15.8 cm) equilibrated with 25 mM TRIS, 300 mM sodium citrate pH 7.0. The column was operated at 180 cm/hr. The column was washed with additional equilibration buffer and the enzyme was eluted with 25 mM TRIS, 75 mM sodium citrate pH 7.0. No enzyme activity was identified in either the flow through or the wash fractions. The main peak contained approximately 75% of the enzyme activity units and the specific activity was calculated to be $2.6 \times 10^6$ U/mg. Based on a column volume of 15.0 mL, the working capacity was calculated to be $5.92 \times 10^6$ U/mL of resin (NEG:010: 111-124). A working capacity was not reported in [mg protein/mL of resin] because the protein load on the column was extremely low following AEX. Additional studies are planned to determine a true loading capacity for the HIC step.

The overall time for the HIC unit operation was shortened dramatically by eliminating the water dilution and increasing the operating flow rate to 240 cm/h from 180 cm/h. Minimizing the exposure time to sodium citrate and the amount of time spent on the resin may ultimately help to reduce the loss of active enzyme. The Q-Sepharose FF output from 1330-D-1003 was diluted with an equal volume of 50 mM TRIS, 0.6 M sodium citrate pH 7.0 and purified using the HIC step elution method described in the paragraph above. The % recovery and specific activity of the main peak (25 mM TRIS, 75 mM sodium citrate pH 7.0) was calculated to be 77% and $2.4 \times 10^6$ U/mg, respectively (NEG:010:125-139). No protein precipitation was observed during or after the dilution with citrate, however the material must be diluted slowly to avoid the "salting-out" phenomenon.

The HIC method was challenged by modifying the salt concentrations of the mobile phases to establish working ranges. The effect on % recovery and enzyme specific activity was investigated by performing two different purification procedures. In the first run, the citrate concentration during loading and elution was decreased while in the second run the citrate concentration during loading was decreased while the citrate concentration in the elution buffer was increased. Q-Sepharose FF output from a 10 L bioreactor run (1330-D-1005) was diluted with an equal volume of 50 mM TRIS, 0.5 M sodium citrate pH 7.0 and loaded onto an HIC column equilibrated with 25 mM TRIS, 250 mM sodium citrate pH 7.0. The column was washed with 25 mM TRIS, 50 mM sodium citrate pH 7.0. Approximately 51% of the enzyme activity was identified in the 50 mM sodium citrate fraction with less than 1% identified in the flow through and the wash fractions. The specific activity of the enzyme in the main peak was calculated to be $1.35 \times 10^6$ U/mg (NEG:010:175-186). In the second HIC run, the Q-Sepharose FF output was diluted and loaded as described above, however 25 mM TRIS, 100 mM sodium citrate pH 7.0 was employed as the elution buffer. In this case, 50% of the enzyme activity was identified in the 100 mM citrate fraction and less than 2% was identified in the flow through and wash fractions. The specific activity of the enzyme in the 100 mM citrate fraction was $2.5 \times 10^6$ U/mg (NEG:010:163-174). The lower specific activity observed in the first HIC run suggested that decreasing the citrate concentration in the elution buffer caused additional proteins that were normally found in the strip to co-elute with the enzyme, thus decreasing the final purity. In contrast, increasing the citrate concentration in the elution buffer did not appear to decrease purity. Based on these data, the concentration of sodium citrate in the elution buffer can vary between 75-100 mM without compromising final purity.

Tangential Flow Filtration No. 2 (TFF 2)

Step Description: TFF 2 is utilized to concentrate and diafilter the Phenyl-Sepharose FF output prior to virus filtration. The HIC output is subjected to TFF immediately to minimize inactivation of the enzyme by prolonged storage in the elution buffer (25 mM TRIS, 75 mM sodium citrate pH 7.0). The Phenyl-Sepharose FF output is concentrated approximately 3-fold and diafiltered to place the enzyme into a suitable buffer for virus filtration and subsequent storage. The TFF 2 step employs a Pellicon 2 Module fitted with a regenerated cellulose PLCTK 30 kDa membrane (Millipore).

Research and Development: The TFF 2 procedure was originally developed for the PAM produced using the B3/A1-7 clone. The enzyme has been shown to be stable in 50 mM TRIS, 25 mM NaCl, 0.0005% TX-100 pH 8.0 under various conditions, for this reason, no additional R&D was attempted.

Figure 12:
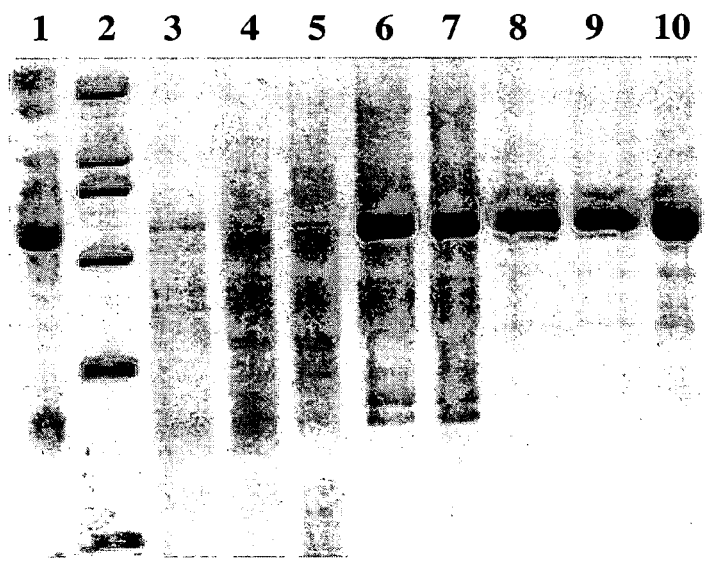
FIG. 12 is a SDS PAGE of purified PAM enzyme.
Figure 13:
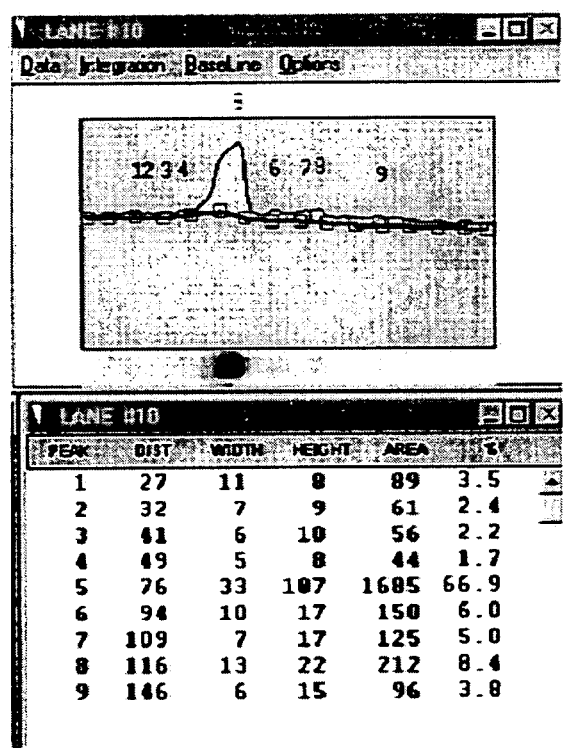
FIG. 13 is a densitometry scan of SDS PAGE gel and calculation of percent peak areas.

Representative Small-Scale Purification of the PAM from C5467 Conditioned CHO Media A sample of conditioned CHO cell media (500 mL) from a 10 L bioreactor run (00107BR, day 15) was concentrated 8-fold and diafiltered against 50 mM TRIS, 0.001% TX-100 pH 8.0. Approximately one-third of the TFF 1 output was purified using a scaled-down version of the purification process described above (NEG:009:219-249). The purification data are summarized in Table 8. The step yields for this purification run were relatively poor and the specific activity of the enzyme actually decreased following the HIC step. However, the SDS-PAGE analysis revealed that overall, α-amidating enzyme was purified to a single major band at approximately 75 kDa (FIG. 12, lane 10). The gel and densitometry scan (FIG. 13) clearly indicated that the enzyme is highly pure (approximate purity, 67%) with only minor low molecular weight impurities present. The enzyme was inactivated over time in many of the purification buffers; therefore the execution of the process must proceed without delay between steps. The variability in the purification process was attributed to the presence of inactive enzyme, which decreases the overall yield and specific activity. More importantly, both the purification and fermentation development preceded concurrently, which may also account for some of the variability observed. Step yields and specific activity at the production scale have subsequently been found to be much better, perhaps as a result of moving the material through the process faster and assaying the fractions promptly.

TABLE 8

Small-Scale Purification Of PAM From UGL 73-26/M Conditioned CHO Media

| Process Step | Yield (U) | Step Yield (%) | Overall Yield (%) | Total Protein (mg) | Specific Activity (U/mg) |
|---|---|---|---|---|---|
| TFF #1 | 5.89E+07 | NA | NA | 36.16 | 1.63E+06 |
| AEX | 3.17E+07 | 53.7 | 53.7 | 7.42 | 4.27E+06 |
| HIC | 1.09E+07 | 34.5 | 18.5 | 4.25 | 2.57E+06 |
| TFF #2 | 8.18E+06 | 74.8 | 13.9 | 2.41 | 3.39E+06 |

Summary of PAM Downstream Purification Process

Purification procedures for each process step that reflect the information that was forwarded to the pilot facility in the technology transfer are detailed below. Data from a representative small-scale purification run, including the SDS-PAGE and densitometry scan, are included in Table 8 and FIGS. 11 and 12.

TFF 1 Procedure: The clarified conditioned CHO cell media is concentrated 5-fold and diafiltered with 50 mM TRIS, 0.001% TX-100 pH 8.0 until a final conductivity of 4-6 mS is achieved. The transmembrane pressure is maintained at ≤10 psi throughout the filtration.

AEX Procedure: The clarified conditioned CHO cell media that has been concentrated/diafiltered by TFF is applied to a Q-Sepharose FF (Amersham Biosciences) column equilibrated with 50 mM TRIS, 120 mM NaCl, 0.001% TX-100 pH 8.0. The column is operated at 180 cm/hr and the UV absorbance is monitored at 280 nm. The column is washed with additional equilibration buffer and the PAM is eluted from the column with 50 mM TRIS, 225 mM NaCl pH 8.0. The column is cleaned with 2.0 M NaCl and sanitized with 1.0 M NaOH. The column is stored between runs in 10 mM NaOH.

HIC Procedure: The Q-Sepharose output is diluted with an equal volume of 50 mM TRIS, 600 mM citrate pH 7.0 and loaded onto a Phenyl-Sepharose FF (Amersham Biosciences) equilibrated with 25 mM TRIS, 300 mM citrate pH 7.0. The column is operated at 240 cm/hr and the UV absorbance is monitored at 280 nm. The column is washed with 25 mM TRIS, 300 mM citrate pH 7.0 and the PAM is eluted from the column with 25 mM TRIS, 75 mM citrate pH 7.0. The column is cleaned and sanitized with 25 mM TRIS pH 7.0 and 1.0 M NaOH, respectively. The column is stored between runs in 10 mM NaOH.

TFF 2 Procedure: The Phenyl-Sepharose FF output is initially concentrated approximately 3-fold, diafiltered with 50 mM TRIS, 25 mM NaCl, 0.0005% TX-100 pH 8.0 and concentrated further to a suitable volume for virus filtration and storage.

10 L Stirred Tank Bioreactor Process Runs

Overview of the 10 L Fermentation and Purification Process for the α-Amidating Enzyme Purified α-AE was prepared following several 10 L stirred tank bioreactor runs. The process steps to derive the α-amidating enzyme were a 14 day inoculum phase, a 17 day fermentation phase and a 2 day purification scheme, detailed above and in FIG. 14. The culture media used in these experiments was a protein-free CHO media, C5467 (Sigma-Aldrich). All process details from these runs can be found in the appropriate batch records.

Figure 14:
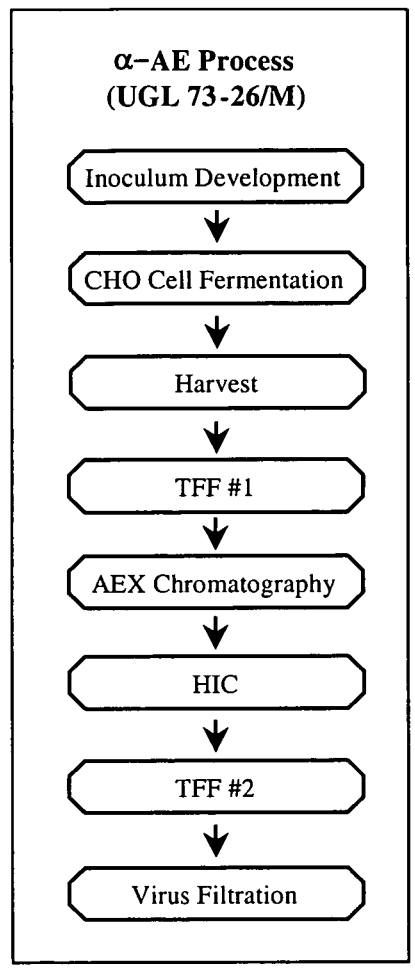
FIG. 14 is a process flow diagram for production of α-AE.

The process flow diagram, FIG. 14, illustrates the final process steps developed for α-AE/PAM produced using the UGL 73-26/M clone.

Phase 1—Inoculum

Figure 15:
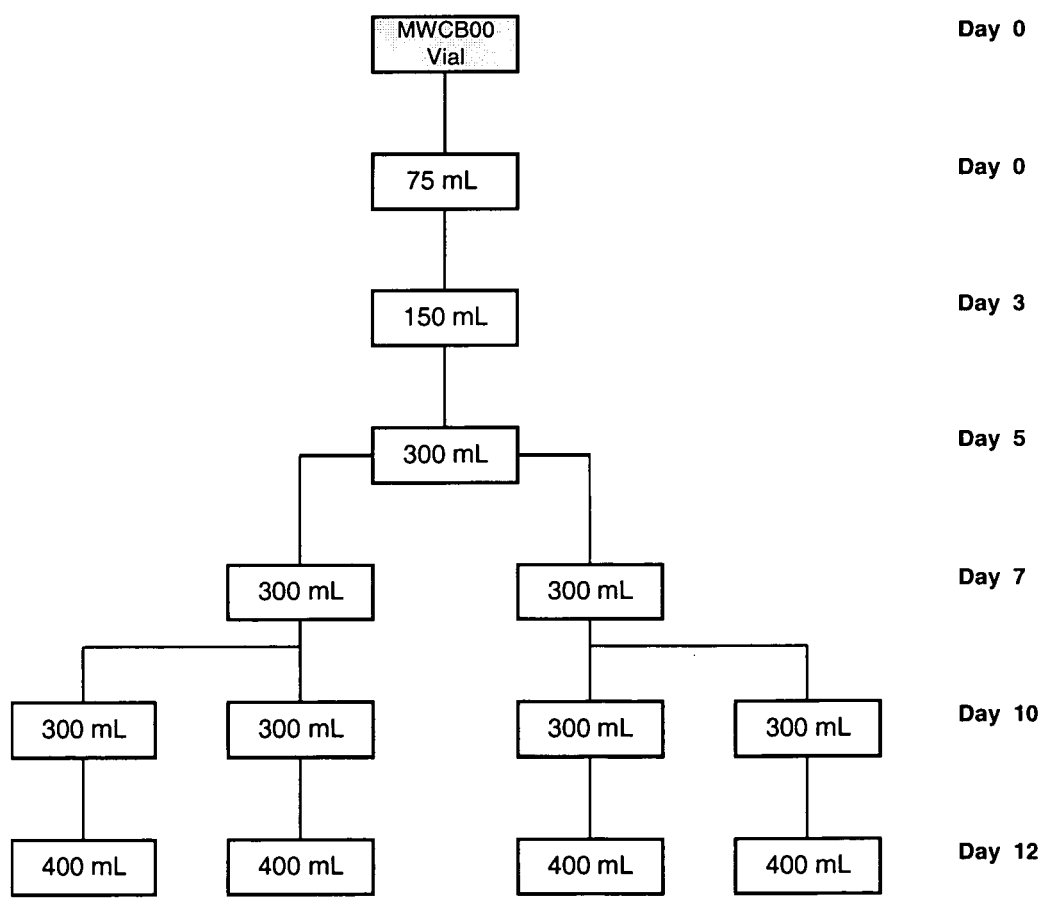
FIG. 15 is an inoculum scheme for UGL 73-26/M.

To prepare an inoculum for a 10 L stirred tank bioreactor a single vial of the UGL 73-26/M MWCB00 was thawed. The cells from the cryovial were removed and place into fresh media. The cell pellet was resuspended into new media and added to a spinner flask containing C5467 CHO media. During the next 14 days the culture was expanded into four flasks containing 400 nL media plus cells (see Inoculum Scheme, FIG. 15).

The culture was tested for α-AE expression at the end of the inoculum phasae 12. On day 12, the average enzyme activity concentration was >13,000 U/mL, see Table 9 panel C. A cell count of the culture and cell viability was done each time the inoculum culture was modified. The culture viability was generally greater than 95% during this phase, see Table 9 panel A. The inoculum culture average total viable cells count was $2.03 \times 10^9$ on day 14, see Table 9 panel B.

TABLE 9

Cell Culture Statistics - Inoculum Phase

| Day of Inoculum | 2130-1003 | 2130-1004 | 2130-1005 | 2130-1006 | 2130-1009 | 2130-1010 | Overall |
|---|---|---|---|---|---|---|---|
| | | | Panel A | | | | |
| | | | Percent Cell Viability (%) | | | | |
| 3 | 98.0 | 97.5 | 100.0 | 98.0 | 98.5 | 98.5 | |
| 5 | 98.5 | 97.5 | 98.5 | 98.0 | 100.0 | 96.5 | |
| 7 | 97.5 | 97.5 | 97.0 | 98.5 | 99.0 | 99.0 | |
| 10A | 98.0 | 99.0 | 98.5 | 97.0 | 99.0 | 98.0 | |
| 10B | 98.0 | 98.0 | 97.5 | 98.5 | 99.0 | 98.5 | |
| 12A | 98.5 | 100.0 | 98.5 | 99.0 | 97.5 | 99.0 | |
| 12B | 98.5 | 100.0 | 99.0 | 100.0 | 98.0 | 99.0 | |
| 12C | 97.5 | 100.0 | 97.0 | 98.5 | 98.5 | 97.5 | |
| 12D | 98.0 | 100.0 | 97.5 | 99.5 | 99.0 | 98.5 | |
| 14A | 97.5 | 100.0 | 93.5 | 97.5 | 100.0 | 95.0 | |
| 14B | 96.5 | 100.0 | 97.5 | 99.5 | 98.0 | 96.0 | |
| 14C | 98.0 | 100.0 | 99.0 | 98.0 | 99.0 | 97.0 | |

TABLE 9-continued

Cell Culture Statistics - Inoculum Phase

| Day of Inoculum | 2130-1003 | 2130-1004 | 2130-1005 | 2130-1006 | 2130-1009 | 2130-1010 | Overall |
|---|---|---|---|---|---|---|---|
| 14D | 96.0 | 100.0 | 98.5 | 97.5 | 98.0 | 97.0 | |
| Day 14 Average | 97.0 | 100.0 | 97.1 | 98.1 | 98.8 | 96.3 | 97.9 |
| SD | | | | | | | 1.7 |

Panel B
Total Number of Viable Cells (×$10^7$)

| | | | | | | | |
|---|---|---|---|---|---|---|---|
| 3 | 3.6 | 1.5 | 1.3 | 2.2 | 1.6 | 2.4 | |
| 5 | 14.7 | 6.3 | 5.7 | 6.1 | 5.5 | 6.3 | |
| 7 | 28.3 | 20.6 | 12.5 | 22.0 | 15.4 | 25.4 | |
| 10A | 34.0 | 38.0 | 29.8 | 38.0 | 32.0 | 40.0 | |
| 10B | 32.0 | 38.0 | 35.6 | 37.0 | 33.0 | 33.0 | |
| 12A | 34.0 | 40.0 | 34.0 | 40.0 | 33.0 | 40.0 | |
| 12B | 29.7 | 44.0 | 32.0 | 41.0 | 32.0 | 34.0 | |
| 12C | 24.0 | 48.0 | 31.0 | 37.0 | 28.0 | 30.0 | |
| 12D | 25.8 | 48.0 | 30.0 | 37.0 | 28.0 | 30.0 | |
| 14A | 38.0 | 67.0 | 56.0 | 48.0 | 44.0 | 45.0 | |
| 14B | 37.0 | 78.0 | 58.0 | 52.0 | 55.0 | 43.0 | |
| 14C | 39.0 | 44.0 | 53.0 | 58.0 | 42.0 | 40.0 | |
| 14D | 30.0 | 70.0 | 72.0 | 60.0 | 49.0 | 40.0 | |
| Day 14 Total | 144.0 | 259.0 | 239.0 | 218.0 | 190.0 | 168.0 | 203.0 |
| SD | | | | | | | 43.7 |

Panel C
Enzyme Activity (U/mL)

| | | | | | | | |
|---|---|---|---|---|---|---|---|
| 12A | 13,112 | 15,630 | 12,301 | 14,408 | 10,093 | 11,951 | |
| 12B | 13,398 | 16,532 | 14,478 | 14,380 | 9,363 | 10,201 | |
| 12C | 13,456 | 16,224 | 13,569 | 15,450 | 9,563 | 11,306 | |
| 12D | 12,905 | 16,057 | 15,568 | 13,014 | 9,490 | 12,183 | |
| Day 12 Average | 13,218 | 16,111 | 13,979 | 14,313 | 9,627 | 11,410 | 13,110 |
| SD | | | | | | | 2,255 |

Phase 2—Fermentation

A 10 L bioreactor was initiated at the completion of each inoculum phase. The bioreactor was seeded at 1×$10^5$ cells/mL in virgin protein-free media with L-glutamine (Sigma, C5467). The bioreactor parameters were set at the following set points; temperature=37° C., RPM=60, pH=no pH set point maintained, the pH was allowed to drift (at the onset, the pH is not allowed to be greater than pH 7.5) and the DO set point is 70% DO. The dissolved oxygen concentration of the virgin media was greater than 70%, the dissolved oxygen concentration of the bioreactor was allowed to drift to 70% and then maintained at that set point. The bioreactor was supplemented with 2 g/L glucose on days 5, 10 and 14. The conditioned media was harvested on day 17. The harvest material was clarified through a Millipore Opticap Filter. The first two fermentations described below were harvested on day 18 instead of day 17, 2131-D-1003 and 2131-D-1004. The maximum cell density of the culture was reached and maintained between days 10 and 17/18. The average maximum cell density from these fermentations was 1.5-1.6×$10^6$ cells/mL, Table 10 panel B. The viability of the culture was >80% for the initial 14 days of culture and the average viability on the day of harvest was 76.0%, Table 10 panel A. The productivity of the culture was evaluated at harvest, day 17/18. The average clarified harvest contained 378,567 units α-AE/mL, Table 10 panel C.

TABLE 10

Cell Culture Statistics - Fermentation Phase

| Day of Fermentation | 2131-1003 | 2131-1004 | 2131-1005 | 2131-1006 | 2131-1009 | 2131-1010 | Average | SD |
|---|---|---|---|---|---|---|---|---|
| Panel A Percent Cell Viability (%) | | | | | | | | |
| 3 | 97.5 | 99.0 | 96.0 | 100.0 | 96.5 | 97.5 | 97.8 | 1.5 |
| 5 | 98.5 | 99.0 | 99.0 | 98.5 | 98.5 | 98.5 | 98.7 | 0.3 |
| 10 | 95.0 | 95.5 | 92.5 | 91.0 | 94.0 | 93.0 | 93.5 | 1.7 |
| 14 | 93.5 | 86.5 | 82.5 | 83.5 | 86.0 | 91.0 | 87.2 | 4.3 |
| 17/18 | 73.5 | 72.5 | 75.0 | 74.5 | 78.5 | 82.0 | 76.0 | 3.6 |
| Panel B Viable Cells Density (cells/mL × $10^6$) | | | | | | | | |
| 3 | 0.4 | 0.3 | 0.4 | 0.4 | 0.3 | 0.3 | 0.4 | 0.1 |
| 5 | 0.6 | 0.6 | 0.8 | 0.7 | 0.8 | 0.4 | 0.7 | 0.1 |
| 10 | 1.2 | 1.3 | 1.9 | 1.9 | 1.4 | 1.5 | 1.5 | 0.3 |

TABLE 10-continued

Cell Culture Statistics - Fermentation Phase

| Day of Fermentation | 2131-1003 | 2131-1004 | 2131-1005 | 2131-1006 | 2131-1009 | 2131-1010 | Average | SD |
|---|---|---|---|---|---|---|---|---|
| 14 | 0.9 | 1.1 | 2.0 | 1.9 | 1.9 | 1.6 | 1.6 | 0.5 |
| 17/18 | 1.4 | 1.3 | 2.0 | 1.4 | 1.9 | 1.5 | 1.6 | 0.3 |

Panel C
Enzyme Activity (U/mL)

| | | | | | | | | |
|---|---|---|---|---|---|---|---|---|
| 17/18 | 412,120 | 398,397 | 371,950 | 505,269 | 383,975 | 319,693 | 378,567 | 61,174 |

Phase 3—Purification

The purification process has 5 distinct steps as detailed above. The clarified harvest was concentrated and diafiltered against 50 mM TRIS, 0.001% TX-100, pH 8.0. The enzyme material was concentrated approximately 4-fold on average (data not shown, see batch records). This process material was applied to a Q-sepharose column and eluted following a NaCl step gradient in a 50 mM TRIS, 0.001% Triton buffer containing 225 mM NaCl. The enzyme solution was diluted with 50 mM TRIS, 600 mM Citrate, pH 7.0 and applied to a phenyl sepharose column. The α-amidating enzyme was eluted from the column following a citrate step gradient. The enzyme material was concentrated to a final volume of approximately 1 L. Four of the six batches of enzyme were processed though a virus removal filter. Two batches were processed through a Millipore NFP filter (1330-D-1005 and 1330-D-1006) and two batches through a Pall Trincor DV50 filter (1330-D-1009 and 1330-D-1010). Data from each of the process steps are shown in Table 11 below.

The first step, TFF 1, was a nearly quantitative step with regard to α-amidating enzyme activity units retention. The TFF concentrate from a 10 L bioreactor run has a mean specific activity of $1.60 \times 10^6$ units/mg protein, Table 11. The TFF 1 concentrate having been applied to a Q-sepharose chromatography column was eluted from the column in approximately 3 L. The specific activity of the enzyme has increased in this process step approximately 2-fold to $3.33 \times 10^6$ units/mg. The protein concentration and enzyme activity concentration of the Q-sepharose eluate were very consistent, see Table 11. Following phenyl-sepharose chromatography the average specific activity of the enzyme increased from $3.33 \times 10^6$ to $4.96 \times 10^6$ units/mg protein. The phenyl-sepharose eluate was concentrated to 1 L using a second TFF step. There is no change in specific activity following this concentration step, Table 11. The TFF 2 concentrates from some enzyme batches were applied to a virus removal filter. The specific activities for 3 of the 4 batches of enzyme decreased, Table 11. The average specific activity for the final purified enzyme decreased 350,000 units/mg to $4.61 \times 10^6$ units/mg protein. The decrease in specific activity was likely to be due to inactivation of some portion of the enzyme.

TABLE 11

Individual Purification Process Step

| Batch # | Enzyme Activity (U/mL) | Protein (mg/mL) | Specific Activity (U/mg) |
|---|---|---|---|
| TFF 1 | | | |
| 1330-D-1003 | 3,575,083 | 1.850 | 1,932,477 |
| 1330-D-1004 | 1,308,056 | 0.572 | 2,286,811 |
| 1330-D-1005 | 1,545,462 | 1.106 | 1,397,344 |
| 1330-D-1006 | 1,560,833 | 1.244 | 1,254,689 |
| 1330-1009 | 1,244,457 | 0.925 | 1,345,359 |
| 1330-1010 | 1,533,800 | 1.481 | 1,035,652 |
| Mean | 1,794,615 | 1.196 | 1,542,055 |
| SD | 882,523 | 0.443 | 470,265 |
| % CV | 49.2 | 37.0 | 30.5 |
| Q Sepharose FF | | | |
| 1330-D-1003 | 710,563 | 0.244 | 2,912,143 |
| 1330-D-1004 | 808,386 | 0.222 | 3,641,378 |
| 1330-D-1005 | 778,492 | 0.255 | 3,052,910 |
| 1330-D-1006 | 816,303 | 0.204 | 4,001,485 |
| 1330-1009 | 778,864 | 0.243 | 3,205,202 |
| 1330-1010 | 807,958 | 0.257 | 3,143,805 |
| Mean | 783,428 | 0.238 | 3,326,154 |
| SD | 39,140 | 0.021 | 412,162 |
| % CV | 5.0 | 8.7 | 12.4 |
| Phenyl Sepharose FF | | | |
| 1330-D-1003 | 274,877 | 0.093 | 2,955,667 |
| 1330-D-1004 | 413,767 | 0.057 | 7,259,070 |
| 1330-D-1005 | 168,186 | 0.029 | 5,799,517 |
| 1330-D-1006 | 296,924 | 0.080 | 3,711,550 |
| 1330-1009 | 357,854 | 0.075 | 4,771,387 |
| 1330-1010 | 325,502 | 0.062 | 5,250,032 |
| Mean | 306,185 | 0.066 | 4,957,871 |
| SD | 83,338 | 0.022 | 1,528,801 |
| % CV | 27.2 | 33.7 | 30.8 |
| TFF 2 | | | |
| 1330-D-1003 | 919,409 | 0.255 | 3,605,525 |
| 1330-D-1004 | 1,325,542 | 0.309 | 4,289,780 |
| 1330-D-1005 | 1,081,522 | 0.220 | 4,916,009 |
| 1330-D-1006 | 1,560,058 | 0.315 | 4,952,565 |
| 1330-1009 | 2,085,104 | 0.363 | 5,744,089 |
| 1330-1010 | 1,423,017 | 0.355 | 4,008,499 |
| Mean | 1,399,109 | 0.303 | 4,586,078 |
| SD | 408,277 | 0.056 | 770,328 |
| % CV | 29.2 | 18.5 | 16.8 |
| Viral Filtration | | | |
| 1330-D-1003 | | | |
| 1330-D-1004 | | | |
| 1330-D-1005 | 989,040 | 0.196 | 5,046,122 |
| 1330-D-1006 | 1,124,322 | 0.298 | 3,772,893 |
| 1330-1009 | 1,528,944 | 0.300 | 5,096,480 |
| 1330-1010 | 1,577,241 | 0.349 | 4,519,315 |
| Mean | 1,304,887 | 0.286 | 4,608,703 |
| SD | 292,541 | 0.064 | 615,313 |
| % CV | 22.4 | 22.5 | 13.4 |

The data illustrating the consistency of each step of a purification process are important. However, just as important is the percent recovery of the desired product at each step of the process. Table 12 shows the percent recovery for each step of the α-amidating enzyme purification process and the overall yield of the process after four or five of the process steps. Table 12 shows that the enzyme was quantitatively recovered from both of the TFF steps. The average percent recoveries for the chromatography steps, Q-sepharose and phenyl sepharose, are 65.3% and 72.0%, respectively. Both of the virus removal filters tested recovered ~80% of the α-AE activity. The overall yield of the enzyme purification process from clarified harvest material through TFF 2 or viral filtration was 40.8% or 38.8%, respectively.

TABLE 12

Cell Culture Statistics - Purification Phase

| Batch # | Purification Process Step (% Recovery) | | | | | Total Recovery Through TFF2 | Total Recovery Through DV50 Viral Filtration |
| --- | --- | --- | --- | --- | --- | --- | --- |
| | TFF 1 | Q-Sepharose | Phenyl-Sepharose | TFF 2 | Viral Filtration | | |
| 1330-D-1003 | 193 | 33 | 37 | 138 | | 33 | |
| 1330-D-1004 | 88 | 87 | 59 | 90 | | 41 | |
| 1330-D-1005 | 117 | 57 | 76 | 79 | 91 | 39 | 36 |
| 1330-D-1006 | 69 | 90 | 80 | 77 | 77 | 38 | 29 |
| 1330-1009 | 95 | 66 | 90 | 92 | 80 | 52 | 42 |
| 1330-1010 | 122 | 59 | 90 | 91 | 114 | 42 | 48 |
| Mean | 114.0 | 65.3 | 72.0 | 94.5 | 90.5 | 40.8 | 38.8 |
| SD | 43.3 | 21.1 | 20.6 | 22.3 | 16.8 | 6.3 | 8.1 |

CONCLUSIONS

A stable well characterized CHO cell line, UGL 73-26/M, that expresses high levels of α-AE activity has been developed. High levels of enzyme expression are achieved in a 17 day batch fermentation process, which utilizes a non-animal source, low protein containing tissue culture medium C5467 (Sigma). Critical fermentation parameters such as pH, DO and glucose concentration have been investigated and optimized. A robust two-step downstream purification process that is capable of purifying the enzyme to near homogeneity has also been developed. The consistency of the fermentation and purification processes are well suited for scale-up to the manufacturing level. Examples are set forth below showing production of amidated product using PAM expressed by cells of the invention.

Example 1

Conversion of Glycine-Extended Parathyroid Hormone Fragment to Amidated Counterpart Using Peptidylglycine α-amidating Monooxygenase Amidation of rhPTH(1-34)Gly35-OH Using Pyruvate The components and final concentrations used for amidation of rhPTH(1-34)Gly35-OH are shown in the Table 12. A brief description of the amidation follows.

TABLE 12

α-Amidation of rhPTH(1-34)Gly35-OH

| Reagent | Final Concentration |
| --- | --- |
| rhPTH(1-34)Gly35-OH | 2 mg/mL |
| 250 mM MES pH 6.3 | 30 mM |
| 3 mM Cupric Sulfate | 0.5 μM |
| 100 mM Sodium Ascorbate | 2 mM |
| Oxygen | The dissolved oxygen concentration is maintained at or near saturation. |
| 400 mM Sodium Pyruvate | 8 mM |
| 250 mM Potassium Iodide | 5 mM |
| 190 Proof Ethanol | 1% |
| PAM | 30,000 U/mL |

Approximately 12.4 grams of rhPTH(1-34)Gly35-OH in 1,900 mL of 25 mM MES, 200 mM NaCl pH 6.0 was charged into a glass vessel fitted with an agitator and gas sparger.
To this solution, the following components were added in the order listed: 3,025 mL water, 741 mL 250 mM MES pH 6.3, 1.03 mL 3 mM cupric sulfate, 124 mL potassium iodide, 62 mL 190 proof ethanol, 124 mL 400 mM sodium pyruvate and 124 mL 100 mM sodium ascorbate.
The reaction vessel was placed into a water-bath and the reaction mixture was heated to 25–27° C. with stirring.
The pH of the reaction mixture was adjusted by to 5.8 with 21 mL of 2 M HCl. Oxygen sparging was initiated; the sparging rate was adjusted to avoid excessive foaming of the reaction mixture.
47 mL of PAM was added and the reaction mixture was incubated at 25–27° C. for 4 hours and 35 minutes (oxygen sparging was performed throughout the incubation period).
The reaction mixture was acidified to pH 2.4 with 74 mL of 2 M HCl.

The PAM enzyme used in this example was expressed from preferred CHO K1 cells of the invention, which were constructed as described supra, and are designated herein as UGL 73-26/M. This cell line was also used to provide the ATCC deposit discussed supra.

The glycine extended precursor may be obtained from known sources, or may be produced in known ways. For example, it may be produced by fermentation in a manner analogous to that described in U.S. Pat. No. 6,103,495 (Examples 1-2 thereof), and purified as described in U.S. Pat. No. 6,103,495 (Example 3 thereof) prior to amidation. The particular precursor used in the present amidation described above was expressed by a cell line of co-pending U.S. patent application Ser. No. 11/076,260, filed Mar. 9, 2005, and published Oct. 6, 2005 as Publication No. US 2005/0221442.

In instances where the enzyme used for amidation is peptidyl glycine alpha-hydroxylating monooxygenase (PHM), the same reaction mixture may be used as that described above, substituting PHM for PAM. In addition, at the end of the 4 to 6 hour incubation period, the pH of the reaction mixture is increased by the addition of base to between 8 and 9. The reaction mixture is agitated for an additional 4 to 8 hours prior to terminating the reaction. PHM may be obtained by expressing PAM as taught herein, followed by separating the PHM catalytic domain from the rest of the PAM molecule. Alternatively, the vectors used herein may be modified to stop translation after PHM but before the PAL catalytic domain. Alternatively, the vector may be constructed, in the first instance, with a PHM coding region in place of the PAM coding region discussed supra. PHM may be obtained by expressing only the N-terminal portion of PAM (about the first 40 kDa). PAMs and the location of their catalytic domains are reported in the literature. Any such PAMs or PHMs are believed useful in accordance with the present invention. See e.g. Mizuno et al, BBRC Vol. 148, No. 2, pp. 546-52 (1987), the disclosure of which is incorporated herein by reference. See especially Mizuno's "AE1." Frog skin is known to express PHM naturally.

Example 2

Post-Amidation Purification

Cation Exchange (CEX) Chromatography

Purification of rhPTH(1-34)-$NH_2$ from residual rhPTH(1-34)Gly35-OH was achieved using CEX chromatography. A brief description of the CEX chromatography method is described below. The acidified amidation output was loaded onto a Toyopearl SP650M (Tosoh Bioscience LLC) column, 9 cm×19 cm, equilibrated with 25 mM MES pH 6.5. The column was operated at 180 cm/hr and the UV absorbance of the column effluent was monitored at 280 nm. The column was washed with 25 mM MES pH 6.5 until the pH of the column effluent pH returned to 6.5. The column was washed with 25 mM MES, 80 mM NaCl pH 6.5 until the wash peak completely eluted and a stable UV baseline was achieved. The product, rhPTH(1-34)-$NH_2$, was eluted from the column with 25 mM MES, 200 mM NaCl pH 6.5. The entire UV peak was collected; fractions were screened by RP-HPLC to determine pooling criteria.

Reversed-Phase (RP) Chromatography

RP chromatography was utilized to exchange the salt form of the peptide from chloride to acetate; RP chromatography provides marginal purification of the peptide. The CEX chromatography output was diluted with 3 volumes of 333 mM sodium acetate and mixed thoroughly. The mixture was allowed to stand for 75 minutes at room temperature prior to loading. The acetate diluted sample was loaded onto a Amberchrom CG300 M (Tosoh Bioscience LLC) column, 6 cm×17 cm, equilibrated with 250 mM sodium acetate pH 7.5. The column was operated at 180 cm/hr and the UV absorbance of the column effluent was monitored at 280 nm. The column was washed with 250 mM sodium acetate pH 7.5 for 60 minutes. The column was equilibrated in 0.1% acetic acid. The product, rhPTH(1-34)-$NH_2$, was eluted from the column with 0.1% acetic acid, 40% ethanol. The entire UV peak was collected.

Characterization of rhPTH(1-34)-$NH_2$

The RP chromatography output was concentrated to a white flocculent powder by lyophilization, yielding 11.8 grams (95% overall yield from amidation) of rhPTH(1-34)-$NH_2$. The molecular mass for rhPTH(1-34)-$NH_2$ was determined to be 4,116.9 Da by electrospray ionization mass spectrometry (ESI-MS), which was consistent with the calculated average molecular mass of 4,116.8 Da.

Although the present invention has been described in relation to particular embodiments thereof, many other variations and modifications and other uses will be apparent to those skilled in the art. The present invention, therefore, is not limited by the specific disclosure herein, but only by the appended claims.

What is claimed is:

1. A CHO K1 cell transfected with an expression vector for expressing peptidylglycine alpha-amidating monooxygenase, wherein said expression vector has a coding region encoding peptidylglycine alpha-amidating monooxygenase, wherein the coding region is operably linked to a control region including a ribosome binding site, a promoter, and an SV40 enhancer upstream of said promoter,
   wherein the promoter is an inducible human metallothionein IIa promoter and is located immediately upstream of a start site of the coding region,
   wherein the SV40 enhancer is located immediately upstream of the inducible human metallothionein IIa promoter,
   wherein the peptidylglycine alpha-amidating monooxygenase consists of a signal peptide at amino acid residues 1 to 25, a pro-region at amino acid residues 26 to 41, and a mature peptidylglycine alpha-amidating monooxygenase at amino acid residues 42 to 715 as set forth in SEQ ID NO: 2,
   wherein the CHO K1 cell is capable of expressing a soluble peptidylglycine alpha-amidating monooxygenase.

2. A recombinant expression vector having a coding region with encoding peptidylglycine alpha-amidating monooxygenase, wherein the coding region is operably linked to a control region including a ribosome binding site, a promoter and an SV40 enhancer upstream of said promoter,
   wherein the promoter is an inducible human metallothionein IIa promoter and is located immediately upstream of a start site of the coding region,
   wherein the SV40 enhancer is located immediately upstream of the inducible human metallothionein IIa promoter,
   wherein the peptidylglycine alpha-amidating monooxygenase consists of a signal peptide at amino acid residues 1 to 25, a pro-region at amino acid residues 26 to 41, and a mature peptidylglycine alpha-amidating monooxygenase at amino acid residues 42 to 715 as set forth in SEQ ID NO: 2,
   wherein the recombinant expression vector is capable of expressing a soluble peptidylglycine alpha-amidating monooxygenase.

3. A method of preparing a cell line for the expression of peptidylglycine alpha-amidating monooxygenase, said method comprising the steps of:
   (A) Transfecting potential host cells in the presence of first, second and third expression vectors, wherein said first vector includes a coding region encoding a first selectable marker, wherein said second vector includes a coding region encoding a second selectable marker, wherein said third vector includes a coding region encoding peptidylglycine alpha-amidating monooxygenase, wherein the coding region is operably linked to a control region including a ribosome binding site, a promoter and an SV40 enhancer upstream of said promoter
   wherein the SV40 enhancer is located immediately upstream of the inducible human metallothionein IIa promoter,
   wherein the peptidylglycine alpha-amidating monooxygenase consists of a signal peptide at amino acid residues 1 to 25, a pro-region at amino acid residues 26 to 41, and a mature peptidylglycine alpha-amidating monooxygenase at amino acid residues 42 to 715 as set forth in SEQ ID NO: 2,
   wherein the third vector is capable of expressing a soluble peptidylglycine alpha-amidating monooxygenase,
   wherein the concentration ratio of said third vector to said first vector is at least 3:1, and wherein the concentration ratio of said third vector to said second vector is at least 3:1;
   (B) Subjecting the cells resulting from step (A) to selectable pressure to select cells that have been transfected with said first vector;
   (C) Subjecting the cells resulting from step (B) to selectable pressure to select cells that have been transfected with said second vector;
   (D) Subjecting the cells resulting from step (C) to limiting dilution and selecting cells expressing soluble peptidylglycine alpha-amidating monooxygenase.

4. The method of claim 3 further comprising the step of amplifying peptidylglycine alpha-amidating monooxygenase by subjecting cells resulting from step (D) to amplifying selective pressure.

5. The method of claim 3 wherein said first selectable marker is a gene encoding neomycin resistance.

6. The method of claim 3 wherein said second selectable marker is a gene encoding dihydrofolate reductase.

7. The method of claim 4 wherein at least one of said selectable markers is a gene encoding dihydrofolate reductase and wherein said amplification is conducted in the presence of methotrexate.

8. The method of claim 3 wherein the concentration ratio of said third vector to said first vector is at least 10:1 and the concentration ratio of said third vector to said second vector is at least 10:1.

9. The method of claim 3 wherein said third vector includes a coding region having nucleic acids encoding peptidylglycine alpha-amidating monooxygenase, operably linked to a control region including a ribosome binding site, a promoter and an SV40 enhancer upstream of said promoter.

10. The method of claim 3 wherein said third vector includes a coding region having nucleic acids encoding peptidylglycine alpha-amidating monooxygenase, operably linked to a control region including a ribosome binding site, human metallothionein to a promoter and an enhancer upstream of said promoter.

11. The method of claim 10 wherein said enhancer is an SV40 enhancer.

12. The method of claim 3 wherein said potential host cells include CHO K1 cells.

13. A cell line that results from the method of claim 3.

14. A cell line comprising host cells transfected with the vector of claim 2.

15. The cell line deposited as ATCC accession number PTA 6784.

* * * * *

SEQUENCE LISTING

```
<160> NUMBER OF SEQ ID NOS: 4

<210> SEQ ID NO 1
<211> LENGTH: 2868
<212> TYPE: DNA
<213> ORGANISM: Rattus norvegicus
<220> FEATURE:
<221> NAME/KEY: CDS
<222> LOCATION: (58)..(2205)

<400> SEQUENCE: 1
gatccatcga tcgcactagt gcccggccac tgcccgctgc cctggtcctg cgcggac        57 atg gcc gga cgc gcc cgc agc ggt ctg cta ctg ctg ctg ctg ggg ctg    105
Met Ala Gly Arg Ala Arg Ser Gly Leu Leu Leu Leu Leu Leu Gly Leu
1               5                   10                  15 ctc gcc ctg cag agc agc tgc ctg gcc ttc aga agc cca ctt tct gtc    153
Leu Ala Leu Gln Ser Ser Cys Leu Ala Phe Arg Ser Pro Leu Ser Val
            20                  25                  30 ttt aag agg ttt aaa gaa act acc aga tca ttt tcc aat gaa tgc ctt    201
Phe Lys Arg Phe Lys Glu Thr Thr Arg Ser Phe Ser Asn Glu Cys Leu
        35                  40                  45 ggt acc att gga cca gtc acc cct ctt gat gca tca gat ttt gcg ctg    249
Gly Thr Ile Gly Pro Val Thr Pro Leu Asp Ala Ser Asp Phe Ala Leu
    50                  55                  60 gat att cgc atg cct ggg gtt aca cct aaa gag tct gac aca tac ttc    297
Asp Ile Arg Met Pro Gly Val Thr Pro Lys Glu Ser Asp Thr Tyr Phe
65                  70                  75                  80
```

```
tgc atg tcc atg cgt ctg cct gtg gat gag gaa gcc ttc gtg att gac      345
Cys Met Ser Met Arg Leu Pro Val Asp Glu Glu Ala Phe Val Ile Asp
                85                  90                  95 ttc aag cct cgt gcc agc atg gat act gtc cac cat atg ctg ctg ttt      393
Phe Lys Pro Arg Ala Ser Met Asp Thr Val His His Met Leu Leu Phe
            100                 105                 110 gga tgc aat atg ccc tcg tcc act gga agt tac tgg ttt tgt gat gaa      441
Gly Cys Asn Met Pro Ser Ser Thr Gly Ser Tyr Trp Phe Cys Asp Glu
        115                 120                 125 gga acc tgt aca gat aaa gcc aat att cta tat gcc tgg gca agg aat      489
Gly Thr Cys Thr Asp Lys Ala Asn Ile Leu Tyr Ala Trp Ala Arg Asn
130                 135                 140 gct ccc ccc acc cgg ctc ccg aaa ggt gtt gga ttc aga gtt gga gga      537
Ala Pro Pro Thr Arg Leu Pro Lys Gly Val Gly Phe Arg Val Gly Gly
145                 150                 155                 160 gaa act gga agc aaa tac ttc gtc ctt caa gtt cac tat ggc gat atc      585
Glu Thr Gly Ser Lys Tyr Phe Val Leu Gln Val His Tyr Gly Asp Ile
                165                 170                 175 agt gct ttt cga gat aat cac aaa gac tgc tct ggc gtg tcc gta cat      633
Ser Ala Phe Arg Asp Asn His Lys Asp Cys Ser Gly Val Ser Val His
            180                 185                 190 ctc aca cgt gtg ccc cag cct tta att gcg ggc atg tac ctt atg atg      681
Leu Thr Arg Val Pro Gln Pro Leu Ile Ala Gly Met Tyr Leu Met Met
        195                 200                 205 tct gtt gac act gtc ata cca cca gga gag aaa gta gtg aat gct gac      729
Ser Val Asp Thr Val Ile Pro Pro Gly Glu Lys Val Val Asn Ala Asp
210                 215                 220 att tcg tgc caa tac aaa atg tat cca atg cat gtg ttt gcc tac aga      777
Ile Ser Cys Gln Tyr Lys Met Tyr Pro Met His Val Phe Ala Tyr Arg
225                 230                 235                 240 gtc cac act cac cat tta ggt aag gtg gtg agc gga tac aga gta aga      825
Val His Thr His His Leu Gly Lys Val Val Ser Gly Tyr Arg Val Arg
                245                 250                 255 aac gga cag tgg aca ctg att gga cgc cag aac ccc cag ctg cca cag      873
Asn Gly Gln Trp Thr Leu Ile Gly Arg Gln Asn Pro Gln Leu Pro Gln
            260                 265                 270 gct ttc tac cct gtg gaa cac ccc gtt gat gtt act ttt ggt gat ata      921
Ala Phe Tyr Pro Val Glu His Pro Val Asp Val Thr Phe Gly Asp Ile
        275                 280                 285 ctg gca gcc aga tgt gtg ttc act ggt gaa ggg agg aca gag gcc acc      969
Leu Ala Ala Arg Cys Val Phe Thr Gly Glu Gly Arg Thr Glu Ala Thr
290                 295                 300 cat atc ggc ggc act tct agt gac gaa atg tgt aac ctg tac atc atg     1017
His Ile Gly Gly Thr Ser Ser Asp Glu Met Cys Asn Leu Tyr Ile Met
305                 310                 315                 320 tat tac atg gaa gcc aaa tat gca ctt tcc ttc atg acc tgt aca aag     1065
Tyr Tyr Met Glu Ala Lys Tyr Ala Leu Ser Phe Met Thr Cys Thr Lys
                325                 330                 335 aac gtg gct cca gat atg ttc aga act atc cca gca gag gcc aat atc     1113
Asn Val Ala Pro Asp Met Phe Arg Thr Ile Pro Ala Glu Ala Asn Ile
            340                 345                 350 cca att cct gtc aaa ccg gac atg gtt atg atg cac ggg cat cac aaa     1161
Pro Ile Pro Val Lys Pro Asp Met Val Met Met His Gly His His Lys
        355                 360                 365 gaa gca gaa aac aaa gaa aag agt gct tta atg cag cag cca aaa cag     1209
Glu Ala Glu Asn Lys Glu Lys Ser Ala Leu Met Gln Gln Pro Lys Gln
370                 375                 380 gga gag gaa gaa gta tta gag cag gat ttc cat gtg gaa gaa gaa ctg     1257
Gly Glu Glu Glu Val Leu Glu Gln Asp Phe His Val Glu Glu Glu Leu
```

-continued

| | |
|---|---|
| gac tgg cct gga gtg tac ttg tta cca ggc cag gtt tct ggg gtg gcc<br>Asp Trp Pro Gly Val Tyr Leu Leu Pro Gly Gln Val Ser Gly Val Ala<br>405 410 415 | 1305 |
| ctg gat tct aag aat aac cta gtg att ttc cac aga ggt gac cat gtt<br>Leu Asp Ser Lys Asn Asn Leu Val Ile Phe His Arg Gly Asp His Val<br>420 425 430 | 1353 |
| tgg gat gga aac tct ttt gac agc aag ttt gtt tac cag caa aga ggt<br>Trp Asp Gly Asn Ser Phe Asp Ser Lys Phe Val Tyr Gln Gln Arg Gly<br>435 440 445 | 1401 |
| ctt ggg cca att gaa gaa gac acc atc ctg gtc att gac cca aat aat<br>Leu Gly Pro Ile Glu Glu Asp Thr Ile Leu Val Ile Asp Pro Asn Asn<br>450 455 460 | 1449 |
| gct gaa atc ctc cag tcc agt ggc aag aac ctg ttt tat tta cca cac<br>Ala Glu Ile Leu Gln Ser Ser Gly Lys Asn Leu Phe Tyr Leu Pro His<br>465 470 475 480 | 1497 |
| ggc ttg agc ata gat aca gat gga aat tat tgg gtc aca gat gtg gct<br>Gly Leu Ser Ile Asp Thr Asp Gly Asn Tyr Trp Val Thr Asp Val Ala<br>485 490 495 | 1545 |
| ctc cac cag gtg ttc aaa ttg gac ccg cat agc aaa gaa ggc cct ctc<br>Leu His Gln Val Phe Lys Leu Asp Pro His Ser Lys Glu Gly Pro Leu<br>500 505 510 | 1593 |
| tta att ctg gga agg agc atg caa cct ggg agt gac caa aat cat ttc<br>Leu Ile Leu Gly Arg Ser Met Gln Pro Gly Ser Asp Gln Asn His Phe<br>515 520 525 | 1641 |
| tgc cag ccc acc gat gtg gct gtg gag ccc agt act gga gct gtc ttc<br>Cys Gln Pro Thr Asp Val Ala Val Glu Pro Ser Thr Gly Ala Val Phe<br>530 535 540 | 1689 |
| gtg tca gac ggt tac tgt aac agt cgg att gtg cag ttt tca cca agc<br>Val Ser Asp Gly Tyr Cys Asn Ser Arg Ile Val Gln Phe Ser Pro Ser<br>545 550 555 560 | 1737 |
| gga aag ttc gtc acc cag tgg gga gaa gag tcc tct gga agc agt cct<br>Gly Lys Phe Val Thr Gln Trp Gly Glu Glu Ser Ser Gly Ser Ser Pro<br>565 570 575 | 1785 |
| agg cca ggc cag ttc agt gtt cct cac agt ttg gcc ctt gtg cct cat<br>Arg Pro Gly Gln Phe Ser Val Pro His Ser Leu Ala Leu Val Pro His<br>580 585 590 | 1833 |
| ttg gac cag ttg tgt gtg gca gac agg gaa aat ggc cga atc caa tgc<br>Leu Asp Gln Leu Cys Val Ala Asp Arg Glu Asn Gly Arg Ile Gln Cys<br>595 600 605 | 1881 |
| ttc aaa act gac acc aaa gaa ttt gtg aga gag att aag cac gca tca<br>Phe Lys Thr Asp Thr Lys Glu Phe Val Arg Glu Ile Lys His Ala Ser<br>610 615 620 | 1929 |
| ttt gga agg aat gtc ttt gcc att tca tat ata cca ggt ttc ctc ttt<br>Phe Gly Arg Asn Val Phe Ala Ile Ser Tyr Ile Pro Gly Phe Leu Phe<br>625 630 635 640 | 1977 |
| gcc gta aac ggg aag cct tac ttt gga gac caa gag ccc gtg caa gga<br>Ala Val Asn Gly Lys Pro Tyr Phe Gly Asp Gln Glu Pro Val Gln Gly<br>645 650 655 | 2025 |
| ttt gtg atg aac ttt tcc agt ggg gaa att ata gac gtc ttc aag cca<br>Phe Val Met Asn Phe Ser Ser Gly Glu Ile Ile Asp Val Phe Lys Pro<br>660 665 670 | 2073 |
| gta cgc aag cac ttc gac atg cct cat gat att gtg gct tct gaa gat<br>Val Arg Lys His Phe Asp Met Pro His Asp Ile Val Ala Ser Glu Asp<br>675 680 685 | 2121 |
| ggg act gtg tac att gga gac gca cac aca aac acc gtg tgg aag ttc<br>Gly Thr Val Tyr Ile Gly Asp Ala His Thr Asn Thr Val Trp Lys Phe<br>690 695 700 | 2169 |
| acc ctg act gaa aaa atg gag cat cgg tca gtc taa aaggctggca | 2215 |

```
Thr Leu Thr Glu Lys Met Glu His Arg Ser Val
705                 710                 715 ttgaagtcca ggaaatcaaa gccgaggcag ttgttgaacc caaagtggag aacaaaccca   2275
cctcctcaga attgcagaag atgcaagaga acagaaaact gagcacagag cccggctcgg   2335
gagtgtccgt ggttctcatt acaacccttc tggttattcc tgtgctggtc ctgctggcca   2395
ttgtcatgtt tattcggtgg aaaaaatcaa gggcctttgg agcagatcat gaccgcaagc   2455
tcgagtcaag ttctggaaga gtcctgggaa gaagaggagg aggaggagga agaagagaag   2515
gaagaggaag agaaggagga gaaaagcag aaggaggaag aagaggagaa ggaggaagat   2575
gaaggcagca ttagccatgg gcagggctct gagaataagt agaaggggaa agggattggc   2635
taagcaccga ttcaaagctg tcagtccttt gggctgcaga tgcaatgtgg ctgcggaatt   2695
ctcatgtttg acagcttatc atcgataagc ttggctgcag gtcaacttgt ttattgcagc   2755
ttataatggt tacaaataaa gcaatagcat cacaaatttc acaaataaag cattttttc    2815 actgcattct agttgtggtt tgtccaaact catcaatgta tcttatcatg tct           2868

<210> SEQ ID NO 2
<211> LENGTH: 715
<212> TYPE: PRT
<213> ORGANISM: Rattus norvegicus

<400> SEQUENCE: 2

Met Ala Gly Arg Ala Arg Ser Gly Leu Leu Leu Leu Leu Gly Leu
1               5                   10                  15

Leu Ala Leu Gln Ser Ser Cys Leu Ala Phe Arg Ser Pro Leu Ser Val
            20                  25                  30

Phe Lys Arg Phe Lys Glu Thr Thr Arg Ser Phe Ser Asn Glu Cys Leu
        35                  40                  45

Gly Thr Ile Gly Pro Val Thr Pro Leu Asp Ala Ser Asp Phe Ala Leu
    50                  55                  60

Asp Ile Arg Met Pro Gly Val Thr Pro Lys Glu Ser Thr Tyr Phe
65                  70                  75                  80

Cys Met Ser Met Arg Leu Pro Val Asp Glu Glu Ala Phe Val Ile Asp
                85                  90                  95

Phe Lys Pro Arg Ala Ser Met Asp Thr Val His His Met Leu Leu Phe
            100                 105                 110

Gly Cys Asn Met Pro Ser Ser Thr Gly Ser Tyr Trp Phe Cys Asp Glu
        115                 120                 125

Gly Thr Cys Thr Asp Lys Ala Asn Ile Leu Tyr Ala Trp Ala Arg Asn
    130                 135                 140

Ala Pro Pro Thr Arg Leu Pro Lys Gly Val Gly Phe Arg Val Gly Gly
145                 150                 155                 160

Glu Thr Gly Ser Lys Tyr Phe Val Leu Gln Val His Tyr Gly Asp Ile
                165                 170                 175

Ser Ala Phe Arg Asp Asn His Lys Asp Cys Ser Gly Val Ser Val His
            180                 185                 190

Leu Thr Arg Val Pro Gln Pro Leu Ile Ala Gly Met Tyr Leu Met Met
        195                 200                 205

Ser Val Asp Thr Val Ile Pro Pro Gly Glu Lys Val Val Asn Ala Asp
    210                 215                 220

Ile Ser Cys Gln Tyr Lys Met Tyr Pro Met His Val Phe Ala Tyr Arg
225                 230                 235                 240

Val His Thr His His Leu Gly Lys Val Val Ser Gly Tyr Arg Val Arg
```

```
                        245                 250                 255
Asn Gly Gln Trp Thr Leu Ile Gly Arg Gln Asn Pro Gln Leu Pro Gln
                260                 265                 270

Ala Phe Tyr Pro Val Glu His Pro Val Asp Val Thr Phe Gly Asp Ile
            275                 280                 285

Leu Ala Ala Arg Cys Val Phe Thr Gly Glu Gly Arg Thr Glu Ala Thr
        290                 295                 300

His Ile Gly Gly Thr Ser Ser Asp Glu Met Cys Asn Leu Tyr Ile Met
305                 310                 315                 320

Tyr Tyr Met Glu Ala Lys Tyr Ala Leu Ser Phe Met Thr Cys Thr Lys
                325                 330                 335

Asn Val Ala Pro Asp Met Phe Arg Thr Ile Pro Ala Glu Ala Asn Ile
            340                 345                 350

Pro Ile Pro Val Lys Pro Asp Met Val Met Met His Gly His His Lys
        355                 360                 365

Glu Ala Glu Asn Lys Glu Lys Ser Ala Leu Met Gln Gln Pro Lys Gln
                370                 375                 380

Gly Glu Glu Glu Val Leu Glu Gln Asp Phe His Val Glu Glu Glu Leu
385                 390                 395                 400

Asp Trp Pro Gly Val Tyr Leu Leu Pro Gly Gln Val Ser Gly Val Ala
                405                 410                 415

Leu Asp Ser Lys Asn Asn Leu Val Ile Phe His Arg Gly Asp His Val
            420                 425                 430

Trp Asp Gly Asn Ser Phe Asp Ser Lys Phe Val Tyr Gln Gln Arg Gly
        435                 440                 445

Leu Gly Pro Ile Glu Glu Asp Thr Ile Leu Val Ile Asp Pro Asn Asn
    450                 455                 460

Ala Glu Ile Leu Gln Ser Ser Gly Lys Asn Leu Phe Tyr Leu Pro His
465                 470                 475                 480

Gly Leu Ser Ile Asp Thr Asp Gly Asn Tyr Trp Val Thr Asp Val Ala
                485                 490                 495

Leu His Gln Val Phe Lys Leu Asp Pro His Ser Lys Glu Gly Pro Leu
            500                 505                 510

Leu Ile Leu Gly Arg Ser Met Gln Pro Gly Ser Asp Gln Asn His Phe
        515                 520                 525

Cys Gln Pro Thr Asp Val Ala Val Glu Pro Ser Thr Gly Ala Val Phe
    530                 535                 540

Val Ser Asp Gly Tyr Cys Asn Ser Arg Ile Val Gln Phe Ser Pro Ser
545                 550                 555                 560

Gly Lys Phe Val Thr Gln Trp Gly Glu Glu Ser Ser Gly Ser Ser Pro
                565                 570                 575

Arg Pro Gly Gln Phe Ser Val Pro His Ser Leu Ala Leu Val Pro His
            580                 585                 590

Leu Asp Gln Leu Cys Val Ala Asp Arg Glu Asn Gly Arg Ile Gln Cys
        595                 600                 605

Phe Lys Thr Asp Thr Lys Glu Phe Val Arg Glu Ile Lys His Ala Ser
    610                 615                 620

Phe Gly Arg Asn Val Phe Ala Ile Ser Tyr Ile Pro Gly Phe Leu Phe
625                 630                 635                 640

Ala Val Asn Gly Lys Pro Tyr Phe Gly Asp Gln Glu Pro Val Gln Gly
                645                 650                 655

Phe Val Met Asn Phe Ser Ser Gly Glu Ile Ile Asp Val Phe Lys Pro
            660                 665                 670
```

-continued

```
Val Arg Lys His Phe Asp Met Pro His Asp Ile Val Ala Ser Glu Asp
        675                 680                 685

Gly Thr Val Tyr Ile Gly Asp Ala His Thr Asn Thr Val Trp Lys Phe
        690                 695                 700

Thr Leu Thr Glu Lys Met Glu His Arg Ser Val
705                 710                 715

<210> SEQ ID NO 3
<211> LENGTH: 23
<212> TYPE: DNA
<213> ORGANISM: Rattus norvegicus

<400> SEQUENCE: 3
gatccatcga tcgcactagt gcc                                       23

<210> SEQ ID NO 4
<211> LENGTH: 16
<212> TYPE: DNA
<213> ORGANISM: Rattus norvegicus

<400> SEQUENCE: 4
actagtgcga tcgatg                                               16
```